United States Patent
Weiner et al.

(10) Patent No.: US 11,524,065 B2
(45) Date of Patent: Dec. 13, 2022

(54) LARGE AND SMALL T ANTIGENS OF MERKEL CELL POLYOMAVIRUS, NUCLEIC ACID CONSTRUCTS AND VACCINES MADE THEREFROM, AND METHODS OF USING SAME

(71) Applicant: THE WISTAR INSTITUTE OF ANATOMY AND BIOLOGY, Philadelphia, PA (US)

(72) Inventors: David B. Weiner, Merion, PA (US); Elizabeth Duperret, Philadelphia, PA (US)

(73) Assignee: THE WISTAR INSTITUTE OF ANATOMY AND BIOLOGY, Philadelphia, PA (US)

( * ) Notice: Subject to any disclaimer, the term of this patent is extended or adjusted under 35 U.S.C. 154(b) by 0 days.

(21) Appl. No.: 16/962,886

(22) PCT Filed: Jan. 18, 2019

(86) PCT No.: PCT/US2019/014171
§ 371 (c)(1),
(2) Date: Jul. 17, 2020

(87) PCT Pub. No.: WO2019/143921
PCT Pub. Date: Jul. 25, 2019

(65) Prior Publication Data
US 2020/0345830 A1    Nov. 5, 2020

Related U.S. Application Data

(60) Provisional application No. 62/619,161, filed on Jan. 19, 2018.

(51) Int. Cl.
*A61K 39/12*    (2006.01)
*A61P 31/20*    (2006.01)
*A61K 39/00*    (2006.01)

(52) U.S. Cl.
CPC .............. *A61K 39/12* (2013.01); *A61P 31/20* (2018.01); *A61K 2039/53* (2013.01); *A61K 2039/572* (2013.01); *A61K 2039/575* (2013.01); *A61K 2039/585* (2013.01)

(58) Field of Classification Search
None
See application file for complete search history.

(56) References Cited

U.S. PATENT DOCUMENTS

| | | |
|---|---|---|
| 2002/0123099 A1 | 9/2002 | Weiner |
| 2020/0345830 A1* | 11/2020 | Weiner .................. A61K 39/12 |

FOREIGN PATENT DOCUMENTS

| | | |
|---|---|---|
| EP | 3101134 | 12/2016 |
| WO | WO 2016/073595 | * 5/2016 |
| WO | 2016193389 | 12/2016 |
| WO | 2017060283 | 4/2017 |

OTHER PUBLICATIONS

Shuda et al. (PNAS. Oct. 2008; 105 (42): 16272-16277).*
Sequence alignments of instant Seq ID Nos. 2, 4, and 6 with UniProt database accession Nos. B6DVW7_9POLY, B0G0V7_9POLY, and B0G0V7_9POLY of Shuda et al. Nov. 2008.*
Seq ID Nos. 2, 4, and 6 alignment with database A_Geneseq_202106 with Barrett et al. WO2016073595.*
Kwun et al. (Journal of Virology; 2015; 89 (8): 4191-4200).*
Sequence alignment of Seq ID No. 1 with Geneseq db acc BDK38670 by Buffat et al. EP3101134 Jan. 2017.*
Zeng et al. (Vaccine; 2012; 30: 1322-1329).*
Spurgeon et al. (Cancers. 2021; 13 (2): 222).*
Tabachnick-Cherny et al. (Molecular Carcinogenesis. 2020; 59: 807-821).*
Gilchuk et al., 2015, "Discovering Protective CD8 T Cell Epitopes—No Single Immunologic Property Predicts It!", Current Opinion in Immunology, 34:43-51.
Gomez et al., 2012, "Strategy for Eliciting Antigen-Specific CD8+ T Cell-Mediated Immune Response Against a Cryptic CTL Epitope of Merkle Cell Polyomavirus Large T Antigen", Cell and Bioscience, 2:36.
Gomez et al., 2013, "Creation of a Merkel Cell Polyomavirus Small T Antigen-Expressing Murine Tumor Model and a DNA Vaccine Targeting Small T Antigen", Cell and Bioscience, 3:29.
Kowalczyk et al., 1999, "Immune Responses to DNA Vaccines", CMLS Cellular and Molecular Life Sciences, 55:751-770.
Kutzler et al., 2008, "DNA Vaccines: Ready for Prime Time?", Nature Reviews Genetics, 9:776-788.
Shuda et al., "Human Merkel cell polyomavirus small T antigen is an oncoprotein targeting the 4E-BP1 translation regulator", J Clin Invest, (Aug. 15, 2011), vol. 121, No. 9, pp. 3623-3634, XP055700171.
Shuda et al., 2011, "Human Merkel Cell Polyomavirus Small T Antigen is an Oncoprotein Targeting the 4E-BP1 Translation Regulator", J Clin Invest, 121:3623-3634.
Spurgeon et al., 2013, "Merkel Cell Polyomavirus: A newly discovered Human Virus with Oncogenic Potential", Virology, 435:18-130.

* cited by examiner

*Primary Examiner* — Shanon A. Foley
(74) *Attorney, Agent, or Firm* — Riverside Law, LLP

(57) ABSTRACT

Nucleic acid molecules and compositions comprising one or more nucleotide sequences that encode a consensus Merkel Cell Polyomavirus (MCV) T antigen. Immunomodulatory methods and methods of inducing an immune response against MCV are disclosed. Method of treating infection by MCV and methods of treating or preventing Merkel Cell Carcinoma associated with MCV are disclosed. Modified consensus MCV T antigens are disclosed.

18 Claims, 15 Drawing Sheets
Specification includes a Sequence Listing.

SEQUENCE LISTING

<160> NUMBER OF SEQ ID NOS: 9

<210> SEQ ID NO 1
<211> LENGTH: 2451
<212> TYPE: DNA
<213> ORGANISM: Artificial Sequence
<220> FEATURE:
<223> OTHER INFORMATION: Nucleotide sequence encoding modified synthetic
      consensus MCV LTAg

<400> SEQUENCE: 1

```
atggacctgg tgctgaacag gaaggagaga gaggccctgt gcaagctgct ggagatcgcc      60
cccaactgtt acggcaatat ccctctgatg aaggccgcct tcaagcggag ctgcctgaag     120
caccacccca acaagggcgg caaccctgtg atcatgatgg agctgaatac cctgtggtcc     180
aagtttcagc agaatatcca caagctgcgg tccgatttct ctatgtttga cgaggtggat     240
gaggccccta tctacggcac caccaagttc aaggagtggt ggcgctccgg cggcttctct     300
tttggcaagg cctacgagta cggccctaac ccacacggca ccaatagcag gtccagaaag     360
ccaagctcca acgccagcag gggagcacca tccggatcta gcccacctca cagccagtcc     420
tctagctccg gctacggctc ttttagcgcc tcccaggcct ctgacagcca gtccagaggc     480
cccgatatcc caccgagca ccacgaggag cctacctcta gctccggctc tagctcccgg     540
gaggagacaa ccaacagcgg cagggagtct agcaccccaa acggcacctc cgtgccaagg     600
aattcctcta ggaccgacgg aaccgccgag gacctgttct gcgataagtc cctgagctcc     660
cctgagcctc catctagctc cgaggagcca gaggagcccc cttctagcag gtcctctccc     720
agacagccac caagctcctc tgccgaggag gcaagctcct ctcagttcac cgacgaggag     780
tacaggagct cctctttac cacccctaag acccctccac ccttctcccg gaagcgcaag     840
tttggaggct ctaggagctc cgcctctagc gcctcctctg ccagcttcac ctccacccct     900
ccaaagccca agaagaacag agagacaccc gtgcctaccg actttcctat cgacctgagc     960
gattacctgt cccacgccgt gtactctaat aagaccgtga gctgtttcgc catctacacc    1020
accagcgaca aggccatcga gctgtacgat aagatcgaga gttcaaggt ggacttcaag    1080 tccaggcacg catgcgagct gggatgtatc ctgctgttca tcaccctgtc caagcaccgc    1140
gtgtctgcca tcaagaactt ctgcagcacc ttttgtacca tctccttct gatctgcaag    1200
```

```
ggcgtgaata agatgcctga gatgtacaac aacctgtgca agccccctta caagctgctg   1260
caggagaaca agccactgct gaattacgag ttccaggaga aggagaagga ggccagctgc   1320
aactggaatc tggtggccga gttcgcctgt gagtacgagc tggacgatca ctttatcatc   1380 ctggccccact acctggactt cgccaagcca tttccctgcc agaagtgtga gaacaggtct   1440
agactgaagc cacacaaggc ccacgaggcc caccactcca atgccaagct gttttacgag   1500
tctaagagcc agaagaccat ctgccagcag gcagcagaca ccgtgctggc aaagaggaga   1560
ctggagatgc tggagatgac caggaccgag atgctgtgca agaagttcaa gaagcacctg   1620
gagcggctgc gcgacctgga taccatcgat ctgctgtact acatgggcgg cgtggcctgg   1680
tactgctgtc tgttcgagga gtttgagaag aagctgcaga agatcatcca gctgctgacc   1740
gagaacatcc aaagtacag aaatatctgg ttcaagggcc ccatcaactc tggcaagacc   1800
agcttcgccg ccgccctgat cgacctgctg gagggcaagg ccctgaacat caattgccct   1860
agcgataagc tgccattcga gctgggctgt gccctggaca agttcatggt ggtgtttgag   1920
gatgtgaagg ccagaactc cctgaataag gacctgcagc ccggcagggg catcaacaat   1980
ctggataacc tgcgggacca cctggatgga gcagtggccg tgagcctgga aagaagcac   2040 gtgaacaaga agcaccagat cttcccaccc tgcatcgtga ccgccaatga ctactttatc   2100
ccaaagaccc tgatcgcccg cttctcttac accctgcact ttagcccaa ggccaacctg   2160 agggacagcc tggatcagaa tatggagatc agaaagaggc gcatcctgca gtccggaacc   2220
accctgctgc tgtgcctgat ctggtgtctg cctgacacca ccttcaagcc atgcctgcag   2280
gaggagatca gaactggaa gcagatcctg cagtctgaga tcagctacgg caagtttttgt   2340 cagatgatcg agaacgtgga ggccggccag gacccctgc tgaatatcct gatcgaggag   2400
gagggcccag aggagacaga ggagacacag gactccggca ccttctctca g             2451

<210> SEQ ID NO 2
<211> LENGTH: 817
<212> TYPE: PRT
<213> ORGANISM: Artificial Sequence
<220> FEATURE:
<223> OTHER INFORMATION: Amino acid sequence of modified synthetic
      consensus MCV LTAg

<400> SEQUENCE: 2

Met Asp Leu Val Leu Asn Arg Lys Glu Arg Glu Ala Leu Cys Lys Leu
1               5                   10                  15

Leu Glu Ile Ala Pro Asn Cys Tyr Gly Asn Ile Pro Leu Met Lys Ala
            20                  25                  30

Ala Phe Lys Ar

-continued

Tyr Gly Ser Phe Ser Ala Ser Gln Ala Ser Asp Ser Gln Ser Arg Gly
145                 150                 155                 160

Pro Asp Ile Pro Pro Glu His His Glu Glu Pro Thr Ser Ser Ser Gly
            165                 170                 175

Ser Ser Ser Arg Glu Glu Thr Thr Asn Ser Gly Arg Glu Ser Ser Thr
            180                 185                 190

Pro Asn Gly Thr Ser Val Pro Arg Asn Ser Ser Arg Thr Asp Gly Thr
            195                 200                 205

Ala Glu Asp Leu Phe Cys Asp Lys Ser Leu Ser Ser Pro Glu Pro Pro
210                 215                 220

Ser Ser Ser Glu Glu Pro Glu Glu Pro Pro Ser Ser Arg Ser Ser Pro
225                 230                 235                 240

Arg Gln Pro Pro Ser Ser Ala Glu Glu Ala Ser Ser Ser Gln Phe
            245                 250                 255

Thr Asp Glu Glu Tyr Arg Ser Ser Phe Thr Thr Pro Lys Thr Pro
            260                 265                 270

Pro Pro Phe Ser Arg Lys Arg Lys Phe Gly Gly Ser Arg Ser Ser Ala
            275                 280                 285

Ser Ser Ala Ser Ser Ala Ser Phe Thr Ser Thr Pro Pro Lys Pro Lys
290                 295                 300

Lys Asn Arg Glu Thr Pro Val Pro Thr Asp Phe Pro Ile Asp Leu Ser
305                 310                 315                 320

Asp Tyr Leu Ser His Ala Val Tyr Ser Asn Lys Thr Val Ser Cys Phe
            325                 330                 335

Ala Ile Tyr Thr Thr Ser Asp Lys Ala Ile Glu Leu Tyr Asp Lys Ile
            340                 345                 350

Glu Lys Phe Lys Val Asp Phe Lys Ser Arg His Ala Cys Glu Leu Gly
            355                 360                 365

Cys Ile Leu Leu Phe Ile Thr Leu Ser Lys His Arg Val Ser Ala Ile
370                 375                 380

Lys Asn Phe Cys Ser Thr Phe Cys Thr Ile Ser Phe Leu Ile Cys Lys
385                 390                 395                 400

Gly Val Asn Lys Met Pro Glu Met Tyr Asn Asn Leu Cys Lys Pro Pro
            405                 410                 415

Tyr Lys Leu Leu Gln Glu Asn Lys Pro Leu Leu Asn Tyr Glu Phe Gln
            420                 425                 430

Glu Lys Glu Lys Glu Ala Ser Cys Asn Trp Asn Leu Val Ala Glu Phe
            435                 440                 445

Ala Cys Glu Tyr Glu Leu Asp Asp His Phe Ile Ile Leu Ala His Tyr
450                 455                 460

Leu Asp Phe Ala Lys Pro Phe Pro Cys Gln Lys Cys Glu Asn Arg Ser
465                 470                 475                 480

Arg Leu Lys Pro His Lys Ala His Glu Ala His His Ser Asn Ala Lys
            485                 490                 495

Leu Phe Tyr Glu Ser Lys Ser Gln Lys Thr Ile Cys Gln Gln Ala Ala
            500                 505                 510

Asp Thr Val Leu Ala Lys Arg Arg Leu Glu Met Leu Glu Met Thr Arg
            515                 520                 525

Thr Glu Met Leu Cys Lys Lys Phe Lys Lys His Leu Glu Arg Leu Arg
            530                 535                 540

Asp Leu Asp Thr Ile Asp Leu Leu Tyr Tyr Met Gly Gly Val Ala Trp
545                 550                 555                 560

-continued

```
Tyr Cys Cys Leu Phe Glu Glu Phe Glu Lys Lys Leu Gln Lys Ile Ile
            565                 570                 575
Gln Leu Leu Thr Glu Asn Ile Pro Lys Tyr Arg Asn Ile Trp Phe Lys
        580                 585                 590
Gly Pro Ile Asn Ser Gly Lys Thr Ser Phe Ala Ala Ala Leu Ile Asp
        595                 600                 605
Leu Leu Glu Gly Lys Ala Leu Asn Ile Asn Cys Pro Ser Asp Lys Leu
        610                 615                 620
Pro Phe Glu Leu Gly Cys Ala Leu Asp Lys Phe Met Val Val Phe Glu
625                 630                 635                 640
Asp Val Lys Gly Gln Asn Ser Leu Asn Lys Asp Leu Gln Pro Gly Gln
                645                 650                 655
Gly Ile Asn Asn Leu Asp Asn Leu Arg Asp His Leu Asp Gly Ala Val
            660                 665                 670
Ala Val Ser Leu Glu Lys Lys His Val Asn Lys His Gln Ile Phe
        675                 680                 685
Pro Pro Cys Ile Val Thr Ala Asn Asp Tyr Phe Ile Pro Lys Thr Leu
        690                 695                 700
Ile Ala Arg Phe Ser Tyr Thr Leu His Phe Ser Pro Lys Ala Asn Leu
705                 710                 715                 720
Arg Asp Ser Leu Asp Gln Asn Met Glu Ile Arg Lys Arg Arg Ile Leu
                725                 730                 735
Gln Ser Gly Thr Thr Leu Leu Leu Cys Leu Ile Trp Cys Leu Pro Asp
            740                 745                 750
Thr Thr Phe Lys Pro Cys Leu Gln Glu Glu Ile Lys Asn Trp Lys Gln
        755                 760                 765
Ile Leu Gln Ser Glu Ile Ser Tyr Gly Lys Phe Cys Gln Met Ile Glu
        770                 775                 780
Asn Val Glu Ala Gly Gln Asp Pro Leu Leu Asn Ile Leu Ile Glu Glu
785                 790                 795                 800
Glu Gly Pro Glu Glu Thr Glu Glu Thr Gln Asp Ser Gly Thr Phe Ser
                805                 810                 815
Gln
```

<210> SEQ ID NO 3
<211> LENGTH: 558
<212> TYPE: DNA
<213> ORGANISM: Artificial Sequence
<220> FEATURE:
<223> OTHER INFORMATION: Nucleotide sequence encoding modified synthetic consensus MCV STAg

<400> SEQUENCE: 3

```
atggacctgg tgctgaaccg aaaggagagg gaggccctgt gcaagctgct ggagatcgcc    60
cctaactgtt acggcaatat cccactgatg aaggccgcct tcaagaggtc ttgcctgaag   120
caccacccaa acaagggcgg caatcccgtg atcatgatgg agctgaacac cctgtggagc   180
aagtttcagc agaatatcca agctgcgcg agcgacttct ccatgtttga tgaggtgagc   240
accaagttcc cctgggagga gtacggaaca gcagcagcag cagcacagtc cggctataac   300
gccaggtttt gcagaggccc tggctgtatg ctgaagcagc tgcgggactc caagtgcgcc   360
tgtatctctt gcaagctgag ccgccagcac tgttctctga agaccctgaa gcagaagaat   420
tgcgccacat ggggcgagtg cttctgttat cagtgtttta tcctgtggtt cggctttccc   480
```

```
cctacatggg agtccttcga ttggtggcag aaaaccctgg aagaaaccga ctactgtctg    540
ctgcatctgc atctgttc                                                 558
```

<210> SEQ ID NO 4
<211> LENGTH: 186
<212> TYPE: PRT
<213> ORGANISM: Artificial Sequence
<220> FEATURE:
<223> OTHER INFORMATION: Amino acid sequence of modified synthetic
      consensus MCV STAg

<400> SEQUENCE: 4

```
Met Asp Leu Val Leu Asn Arg Lys Glu Arg Glu Ala Leu Cys Lys Leu
1               5                   10                  15

Leu Glu Ile Ala Pro Asn Cys Tyr Gly Asn Ile Pro Leu Met Lys Ala
            20                  25                  30

Ala Phe Lys Arg Ser Cys Leu Lys His His Pro Asn Lys Gly Gly Asn
        35                  40                  45

Pro Val Ile Met Met Glu Leu Asn Thr Leu Trp Ser Lys Phe Gln Gln
    50                  55                  60

Asn Ile His Lys Leu Arg Ser Asp Phe Ser Met Phe Asp Glu Val Ser
65                  70                  75                  80

Thr Lys Phe Pro Trp Glu Glu Tyr Gly Thr Ala Ala Ala Ala Ala Gln
                85                  90                  95

Ser Gly Tyr Asn Ala Arg Phe Cys Arg Gly Pro Gly Cys Met Leu Lys
            100                 105                 110

Gln Leu Arg Asp Ser Lys Cys Ala Cys Ile Ser Cys Lys Leu Ser Arg
        115                 120                 125

Gln His Cys Ser Leu Lys Thr Leu Lys Gln Lys Asn Cys Ala Thr Trp
    130                 135                 140

Gly Glu Cys Phe Cys Tyr Gln Cys Phe Ile Leu Trp Phe Gly Phe Pro
145                 150                 155                 160

Pro Thr Trp Glu Ser Phe Asp Trp Trp Gln Lys Thr Leu Glu Glu Thr
                165                 170                 175

Asp Tyr Cys Leu Leu His Leu His Leu Phe
            180                 185
```

<210> SEQ ID NO 5
<211> LENGTH: 3027
<212> TYPE: DNA
<213> ORGANISM: Artificial Sequence
<220> FEATURE:
<223> OTHER INFORMATION: Nucleotide sequence encoding modified synthetic
      consensus LTAg and STAg linked with a furin cleavage site

<400> SEQUENCE: 5

```
atggacctgg tgctgaacag gaaggagaga gaggccctgt gcaagctgct ggagatcgcc    60
cccaactgtt acggcaatat ccctctgatg aaggccgcct tcaagcggag ctgcctgaag   120
caccacccca caagggcgg caaccctgtg atcatgatgg agctgaatac cctgtggtcc    180
aagtttcagc agaatatcca caagctgcgg tccgatttct ctatgtttga cgaggtggat    240
gaggccccta tctacggcac caccaagttc aaggagtggg gcgctccgg cggcttctct    300 tttggcaagg cctacgagta cggccctaac ccacacggca ccaatagcag gtccagaaag    360
ccaagctcca cgccagcag gggagcacca tccggatcta gcccacctca cagccagtcc    420
tctagctccg gctacggctc ttttagcgcc tcccaggcct tgacagcca gtccagaggc    480 cccgatatcc caccgagca ccacgaggag cctacctcta gctccggctc tagctccgg    540
```

```
gaggagacaa ccaacagcgg cagggagtct agcaccccaa acggcacctc cgtgccaagg    600
aattcctcta ggaccgacgg aaccgccgag gacctgttct gcgataagtc cctgagctcc    660
cctgagcctc catctagctc cgaggagcca gaggagcccc cttctagcag gtcctctccc    720
agacagccac caagctcctc tgccgaggag gcaagctcct ctcagttcac cgacgaggag    780
tacaggagct cctcttttac caccccctaag accccctccac ccttctcccg gaagcgcaag    840
tttggaggct ctaggagctc cgcctctagc gcctcctctg ccagcttcac ctccacccct    900
ccaaagccca agaagaacag agagacaccc gtgcctaccg actttcctat cgacctgagc    960
gattacctgt cccacgccgt gtactctaat aagaccgtga gctgtttcgc catctacacc   1020
accagcgaca aggccatcga gctgtacgat aagatcgaga agttcaaggt ggacttcaag   1080
tccaggcacg catgcgagct gggatgtatc ctgctgttca tcaccctgtc caagcaccgc   1140
gtgtctgcca tcaagaactt ctgcagcacc ttttgtacca tctcctttct gatctgcaag   1200
ggcgtgaata gatgcctga gatgtacaac aacctgtgca agccccctta caagctgctg   1260
caggagaaca agccactgct gaattacgag ttccaggaga aggagaagga ggccagctgc   1320
aactggaatc tggtggccga gttcgcctgt gagtacgagc tggacgatca ctttatcatc   1380
ctggcccact acctggactt cgccaagcca tttccctgcc agaagtgtga aacaggtct   1440 agactgaagc cacacaaggc ccacgaggcc caccactcca atgccaagct gttttacgag   1500
tctaagagcc agaagaccat ctgccagcag gcagcagaca ccgtgctggc aaagaggaga   1560
ctggagatgc tggagatgac caggaccgag atgctgtgca agaagttcaa gaagcacctg   1620
gagcggctgc gcgacctgga taccatcgat ctgctgtact acatgggcgg cgtggcctgg   1680
tactgctgtc tgttcgagga gtttgagaag aagctgcaga agatcatcca gctgctgacc   1740
gagaacatcc caaagtacag aaatatctgg ttcaagggcc ccatcaactc tggcaagacc   1800
agcttcgccg ccgccctgat cgacctgctg gagggcaagg ccctgaacat caattgccct   1860
agcgataagc tgccattcga gctgggctgt gccctggaca agttcatggt ggtgtttgag   1920
gatgtgaagg ccagaactc cctgaataag gacctgcagc ccggccaggg catcaacaat   1980
ctggataacc tgcgggacca cctggatgga gcagtggccg tgagcctgga gaagaagcac   2040
gtgaacaaga agcaccagat cttcccaccc tgcatcgtga ccgccaatga ctactttatc   2100
ccaaagaccc tgatcgcccg cttctcttac accctgcact ttagccccaa ggccaacctg   2160
agggacagcc tggatcagaa tatggagatc agaaagaggc gcatcctgca gtccggaacc   2220
accctgctgc tgtgcctgat ctggtgtctg cctgacacca ccttcaagcc atgcctgcag   2280
gaggagatca agaactggaa gcagatcctg cagtctgaga tcagctacgg caagttttgt   2340
cagatgatcg agaacgtgga ggccggccag gaccccctgc tgaatatcct gatcgaggag   2400
gagggcccag aggagacaga ggagacacag gactccggca ccttctctca gagaggccgc   2460
aaaaggaggt ctgatctggt gctgaatcgg aaagagagag aagccctgtg caaactgctg   2520
gaaatcgccc caaactgtta cggcaacatc cccctgatga aggccgcctt caagaggtct   2580
tgcctgaagc accacccaaa caagggcggc aatcccgtga tcatgatgga gctgaacacc   2640
ctgtggagca gtttcagca gaatatccac aagctgcgga gcgacttctc catgtttgat   2700
gaggtgagca ccaagttccc ttgggaggag tacggaacag cagcagcagc agcacagtcc   2760
ggctataacg ccaggttttg cagaggccca ggctgtatgc tgaagcagct gcgggactcc   2820
aagtgcgcct gtatctcttg caagctgagc cgccagcact gttctctgaa gaccctgaag   2880
cagaagaatt gcgccacatg gggcgagtgc ttctgttatc agtgttttat cctgtggttc   2940
```

-continued

```
ggctttcccc ctacatggga gtccttcgat tggtggcaga aaaccctgga ggaaactgat    3000
tactgtctgc tgcacctgca cctgttc                                        3027
```

<210> SEQ ID NO 6
<211> LENGTH: 1009
<212> TYPE: PRT
<213> ORGANISM: Artificial Sequence
<220> FEATURE:
<223> OTHER INFORMATION: Amino acid sequence of modified synthetic
      consensus LTAg and STAg linked with a furin cleavage site

<400> SEQUENCE: 6

```
Met Asp Leu Val Leu Asn Arg Lys Glu Arg Glu Ala Leu Cys Lys Leu
1               5                   10                  15

Leu Glu Ile Ala Pro Asn Cys Tyr Gly Asn Ile Pro Leu Met Lys Ala
            20                  25                  30

Ala Phe Lys Arg Ser Cys Leu Lys His His Pro Asn Lys Gly Gly Asn
        35                  40                  45

Pro Val Ile Met Met Glu Leu Asn Thr Leu Trp Ser Lys Phe Gln Gln
    50                  55                  60

Asn Ile His Lys Leu Arg Ser Asp Phe Ser Met Phe Asp Glu Val Asp
65                  70                  75                  80

Glu Ala Pro Ile Tyr Gly Thr Thr Lys Phe Lys Glu Trp Trp Arg Ser
                85                  90                  95

Gly Gly Phe Ser Phe Gly Lys Ala Tyr Glu Tyr Gly Pro Asn Pro His
            100                 105                 110

Gly Thr Asn Ser Arg Ser Arg Lys Pro Ser Ser Asn Ala Ser Arg Gly
        115                 120                 125

Ala Pro Ser Gly Ser Ser Pro His Ser Gln Ser Ser Ser Ser Gly
    130                 135                 140

Tyr Gly Ser Phe Ser Ala Ser Gln Ala Ser Asp Ser Gln Ser Arg Gly
145                 150                 155                 160

Pro Asp Ile Pro Pro Glu His His Glu Glu Pro Thr Ser Ser Ser Gly
                165                 170                 175

Ser Ser Ser Arg Glu Glu Thr Thr Asn Ser Gly Arg Glu Ser Ser Thr
            180                 185                 190

Pro Asn Gly Thr Ser Val Pro Arg Asn Ser Ser Arg Thr Asp Gly Thr
        195                 200                 205

Ala Glu Asp Leu Phe Cys Asp Lys Ser Leu Ser Ser Pro Glu Pro Pro
    210                 215                 220

Ser Ser Ser Glu Glu Pro Glu Glu Pro Ser Ser Arg Ser Ser Pro
225                 230                 235                 240

Arg Gln Pro Pro Ser Ser Ala Glu Glu Ala Ser Ser Ser Gln Phe
                245                 250                 255

Thr Asp Glu Glu Tyr Arg Ser Ser Ser Phe Thr Thr Pro Lys Thr Pro
            260                 265                 270

Pro Pro Phe Ser Arg Lys Arg Lys Phe Gly Gly Ser Arg Ser Ser Ala
        275                 280                 285

Ser Ser Ala Ser Ser Ala Ser Phe Thr Ser Thr Pro Pro Lys Pro Lys
    290                 295                 300

Lys Asn Arg Glu Thr Pro Val Pro Thr Asp Phe Pro Ile Asp Leu Ser
305                 310                 315                 320

Asp Tyr Leu Ser His Ala Val Tyr Ser Asn Lys Thr Val Ser Cys Phe
                325                 330                 335
```

```
Ala Ile Tyr Thr Thr Ser Asp Lys Ala Ile Glu Leu Tyr Asp Lys Ile
                340                 345                 350

Glu Lys Phe Lys Val Asp Phe Lys Ser Arg His Ala Cys Glu Leu Gly
            355                 360                 365

Cys Ile Leu Leu Phe Ile Thr Leu Ser Lys His Arg Val Ser Ala Ile
        370                 375                 380

Lys Asn Phe Cys Ser Thr Phe Cys Thr Ile Ser Phe Leu Ile Cys Lys
385                 390                 395                 400

Gly Val Asn Lys Met Pro Glu Met Tyr Asn Asn Leu Cys Lys Pro Pro
                405                 410                 415

Tyr Lys Leu Leu Gln Glu Asn Lys Pro Leu Leu Asn Tyr Glu Phe Gln
            420                 425                 430

Glu Lys Glu Lys Glu Ala Ser Cys Asn Trp Asn Leu Val Ala Glu Phe
        435                 440                 445

Ala Cys Glu Tyr Glu Leu Asp Asp His Phe Ile Ile Leu Ala His Tyr
    450                 455                 460

Leu Asp Phe Ala Lys Pro Phe Pro Cys Gln Lys Cys Glu Asn Arg Ser
465                 470                 475                 480

Arg Leu Lys Pro His Lys Ala His Glu Ala His His Ser Asn Ala Lys
                485                 490                 495

Leu Phe Tyr Glu Ser Lys Ser Gln Lys Thr Ile Cys Gln Gln Ala Ala
            500                 505                 510

Asp Thr Val Leu Ala Lys Arg Arg Leu Glu Met Leu Glu Met Thr Arg
        515                 520                 525

Thr Glu Met Leu Cys Lys Lys Phe Lys Lys His Leu Glu Arg Leu Arg
    530                 535                 540

Asp Leu Asp Thr Ile Asp Leu Leu Tyr Tyr Met Gly Gly Val Ala Trp
545                 550                 555                 560

Tyr Cys Cys Leu Phe Glu Glu Phe Glu Lys Lys Leu Gln Lys Ile Ile
                565                 570                 575

Gln Leu Leu Thr Glu Asn Ile Pro Lys Tyr Arg Asn Ile Trp Phe Lys
            580                 585                 590

Gly Pro Ile Asn Ser Gly Lys Thr Ser Phe Ala Ala Ala Leu Ile Asp
        595                 600                 605

Leu Leu Glu Gly Lys Ala Leu Asn Ile Asn Cys Pro Ser Asp Lys Leu
    610                 615                 620

Pro Phe Glu Leu Gly Cys Ala Leu Asp Lys Phe Met Val Val Phe Glu
625                 630                 635                 640

Asp Val Lys Gly Gln Asn Ser Leu Asn Lys Asp Leu Gln Pro Gly Gln
                645                 650                 655

Gly Ile Asn Asn Leu Asp Asn Leu Arg Asp His Leu Asp Gly Ala Val
            660                 665                 670

Ala Val Ser Leu Glu Lys Lys His Val Asn Lys His Gln Ile Phe
        675                 680                 685

Pro Pro Cys Ile Val Thr Ala Asn Asp Tyr Phe Ile Pro Lys Thr Leu
    690                 695                 700

Ile Ala Arg Phe Ser Tyr Thr Leu His Phe Ser Pro Lys Ala Asn Leu
705                 710                 715                 720

Arg Asp Ser Leu Asp Gln Asn Met Glu Ile Arg Lys Arg Arg Ile Leu
                725                 730                 735

Gln Ser Gly Thr Thr Leu Leu Leu Cys Leu Ile Trp Cys Leu Pro Asp
            740                 745                 750
```

```
Thr Thr Phe Lys Pro Cys Leu Gln Glu Ile Lys Asn Trp Lys Gln
        755                 760                 765

Ile Leu Gln Ser Glu Ile Ser Tyr Gly Lys Phe Cys Gln Met Ile Glu
    770                 775                 780

Asn Val Glu Ala Gly Gln Asp Pro Leu Leu Asn Ile Leu Ile Glu Glu
785                 790                 795                 800

Glu Gly Pro Glu Glu Thr Glu Thr Gln Asp Ser Gly Thr Phe Ser
                805                 810                 815

Gln Arg Gly Arg Lys Arg Ser Asp Leu Val Leu Asn Arg Lys Glu
            820                 825                 830

Arg Glu Ala Leu Cys Lys Leu Leu Glu Ile Ala Pro Asn Cys Tyr Gly
        835                 840                 845

Asn Ile Pro Leu Met Lys Ala Ala Phe Lys Arg Ser Cys Leu Lys His
    850                 855                 860

His Pro Asn Lys Gly Gly Asn Pro Val Ile Met Met Glu Leu Asn Thr
865                 870                 875                 880

Leu Trp Ser Lys Phe Gln Gln Asn Ile His Lys Leu Arg Ser Asp Phe
                885                 890                 895

Ser Met Phe Asp Glu Val Ser Thr Lys Phe Pro Trp Glu Glu Tyr Gly
            900                 905                 910

Thr Ala Ala Ala Ala Gln Ser Gly Tyr Asn Ala Arg Phe Cys Arg
        915                 920                 925

Gly Pro Gly Cys Met Leu Lys Gln Leu Arg Asp Ser Lys Cys Ala Cys
    930                 935                 940

Ile Ser Cys Lys Leu Ser Arg Gln His Cys Ser Leu Lys Thr Leu Lys
945                 950                 955                 960

Gln Lys Asn Cys Ala Thr Trp Gly Glu Cys Phe Cys Tyr Gln Cys Phe
                965                 970                 975

Ile Leu Trp Phe Gly Phe Pro Pro Thr Trp Glu Ser Phe Asp Trp Trp
            980                 985                 990

Gln Lys Thr Leu Glu Glu Thr Asp  Tyr Cys Leu Leu His  Leu His Leu
        995                 1000                1005

Phe

<210> SEQ ID NO 7
<211> LENGTH: 18
<212> TYPE: PRT
<213> ORGANISM: Artificial Sequence
<220> FEATURE:
<223> OTHER INFORMATION: Amino acid sequence of IgE leader sequence

<400> SEQUENCE: 7

Met Asp Trp Thr Trp Ile Leu Phe Leu Val Ala Ala Thr Arg Val
1               5                   10                  15

His Ser

<210> SEQ ID NO 8
<211> LENGTH: 5
<212> TYPE: PRT
<213> ORGANISM: Artificial Sequence
<220> FEATURE:
<223> OTHER INFORMATION: Chemically synthesized

<400> SEQUENCE: 8

Leu Lys Asp Tyr Met
1               5
```

```
<210> SEQ ID NO 9
<211> LENGTH: 5
<212> TYPE: PRT
<213> ORGANISM: Artificial Sequence
<220> FEATURE:
<223> OTHER INFORMATION: Chemically synthesized

<400> SEQUENCE: 9

Ala Ala Ala Ala Ala
1               5
```

LARGE AND SMALL T ANTIGENS OF MERKEL CELL POLYOMAVIRUS, NUCLEIC ACID CONSTRUCTS AND VACCINES MADE THEREFROM, AND METHODS OF USING SAME

CROSS-REFERENCE TO RELATED APPLICATIONS

This application is a U.S. national phase application filed under 35 U.S.C. § 371 claiming priority to International Patent Application No. PCT/US19/14171, filed Jan. 18, 2019, which is entitled to priority under 35 U.S.C. § 119(e) to U.S. Provisional Patent Application No. 62/619,161, filed Jan. 19, 2018, the contents of each of which are incorporated by reference herein in their entireties.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: 206194-0021-00US_SubstituteSequenceListing.txt; created on Dec. 16, 2021, and having a size of 27,273, is hereby incorporated by reference.

FIELD OF THE INVENTION

The present invention relates to vaccines for inducing immune responses and treating individuals infected with MCV and/or treating or preventing Merkel Cell Carcinoma (MCC). The present invention relates to consensus MCV large T antigen (LTAg) and small t antigen (STAg) oncoproteins and nucleic acid molecules which encode the same.

BACKGROUND OF THE INVENTION

Merkel Cell Polyomavirus (MCV) has gained recent attention due to its link with Merkel Cell Carcinoma (MCC), an aggressive human skin cancer. Approximately 1,500 new cases of MCC are diagnosed per year in the United States, and the mortality rate for subjects with MCC remains at 46%. MCC kills more patients than cutaneous T cell lymphoma and chronic myeloid leukemia. A majority (approximately 75%) of MCCs contain clonally integrated viral DNA and express viral T antigen transcripts and protein.

Currently there are no vaccines against MCC being tested in clinical trials. Therefore, there is need in the art for therapeutic vaccines against MCV and MCC. The current invention satisfies this unmet need.

SUMMARY OF THE INVENTION

In one embodiment, the invention relates to an immunogenic composition comprising a nucleic acid molecule encoding at least one modified Merkel Cell Polyomavirus (MCV) T antigen, wherein the T antigen comprises at least one mutation that disrupts at least one oncogenic feature of a native MCV T antigen. In one embodiment, the at least one oncogenic feature is at least one of CR1 binding, DnaJ binding, phophatase pp2A-binding binding, Rb binding, ATPase activity, helicase activity, chaperone protein binding, hVam6p binding, Fbxw7 binding, origin binding, and transformation.

In one embodiment, the at least one mutation is a mutation at an amino acid at least one of D44, W209, E216, L142, L91, K92, D93, Y94 or M95. In one embodiment, the at least one mutation is at least one of a D44N mutation, a W209A, an E216K mutation, an L142A mutation, an L91A mutation, a K92A mutation, a D93A mutation, a Y94A mutation or a M95A mutation. In one embodiment, the modified MCV T antigen comprises at least one of a D44N mutation, a W209A, or an E216K mutation. In one embodiment, the modified MCV T comprises a D44N mutation, a W209A, and an E216K mutation.

In one embodiment, the at least one MCV T antigen is a large T antigen (LTAg) or a small t antigen (STAg.) In one embodiment, the at least one MCV T antigen is a combination of a LTAg and a STAg.

In one embodiment, the nucleic acid molecule encodes a peptide comprising an amino acid sequence of a) an amino acid sequence having at least about 90% identity over an entire length of the amino acid sequence to at least one of SEQ ID NO:2, SEQ ID NO:4 or SEQ ID NO:6, b) an immunogenic fragment comprising at least about 90% identity over at least 60% of the amino acid sequence to at least one of SEQ ID NO:2, SEQ ID NO:4 or SEQ ID NO:6, c) the amino acid sequence of SEQ ID NO:2, SEQ ID NO:4 or SEQ ID NO:6, or d) an immunogenic fragment comprising at least 60% of the amino acid sequence of SEQ ID NO:2, SEQ ID NO:4 or SEQ ID NO:6.

In one embodiment, the nucleic acid molecule is a DNA molecule or a RNA molecule.

In one embodiment, the nucleic acid molecule comprises a nucleotide sequence at least one of a) a nucleotide sequence having at least about 90% identity over an entire length of a nucleotide sequence to at least one of SEQ ID NO:1, SEQ ID NO:3 or SEQ ID NO:5, b) an immunogenic fragment of a nucleotide sequence having at least about 90% identity over at least 60% of the nucleotide sequence to at least one of SEQ ID NO:1, SEQ ID NO:3 or SEQ ID NO:5, c) a nucleotide sequence of SEQ ID NO:1, SEQ ID NO:3 or SEQ ID NO:5, or d) an immunogenic fragment of a nucleotide sequence of SEQ ID NO:1, SEQ ID NO:3 or SEQ ID NO:5.

In one embodiment, the nucleotide sequence encoding the peptide is operably linked to at least one regulatory sequence. In one embodiment, the regulatory sequence is at least one of a start codon, an IgE leader sequence or a stop codon.

In one embodiment, the nucleic acid molecule encodes a peptide comprising an amino acid sequence of at least one of a) an amino acid sequence having at least about 90% identity over an entire length of the amino acid sequence to at least one of SEQ ID NO:2, SEQ ID NO:4 or SEQ ID NO:6, b) an immunogenic fragment comprising at least about 90% identity over at least 60% of the amino acid sequence to at least one of SEQ ID NO:2, SEQ ID NO:4 or SEQ ID NO:6, c) the amino acid sequence of SEQ ID NO:2, SEQ ID NO:4 or SEQ ID NO:6, or d) an immunogenic fragment comprising at least 60% of the amino acid sequence of SEQ ID NO:2, SEQ ID NO:4 or SEQ ID NO:6, operably linked to an amino acid sequence as set forth in SEQ ID NO:7.

In one embodiment, the nucleic acid molecule comprises a nucleotide sequence of at least one of a) a nucleotide sequence having at least about 90% identity over an entire length of a nucleotide sequence to at least one of SEQ ID NO:1, SEQ ID NO:3 or SEQ ID NO:5, b) an immunogenic fragment of a nucleotide sequence having at least about 90% identity over at least 60% of the nucleotide sequence to at least one of SEQ ID NO:1, SEQ ID NO:3 or SEQ ID NO:5, c) a nucleotide sequence of SEQ ID NO:1, SEQ ID NO:3 or SEQ ID NO:5, or d) an immunogenic fragment of a nucleotide sequence of SEQ ID NO:1, SEQ ID NO:3 or SEQ ID NO:5, operably linked to an nucleotide sequence encoding SEQ ID NO:7.

In one embodiment, the nucleic acid molecule comprises an expression vector.

In one embodiment, the nucleic acid molecule is incorporated into a viral particle.

In one embodiment, the immunogenic composition further comprises a pharmaceutically acceptable excipient.

In one embodiment, the immunogenic composition further comprises an adjuvant.

In one embodiment, the invention relates to a nucleic acid molecule encoding a peptide comprising an amino acid sequence of at least one of a) an amino acid sequence having at least about 90% identity over an entire length of the amino acid sequence to at least one of SEQ ID NO:2, SEQ ID NO:4 or SEQ ID NO:6, b) an immunogenic fragment comprising at least about 90% identity over at least 60% of the amino acid sequence to at least one of SEQ ID NO:2, SEQ ID NO:4 or SEQ ID NO:6, c) the amino acid sequence of SEQ ID NO:2, SEQ ID NO:4 or SEQ ID NO:6, or d) an immunogenic fragment comprising at least 60% of the amino acid sequence of SEQ ID NO:2, SEQ ID NO:4 or SEQ ID NO:6.

In one embodiment, the nucleic acid molecule is a DNA molecule or a RNA molecule.

In one embodiment, the nucleic acid molecule comprises a nucleotide sequence at least one of a) a nucleotide sequence having at least about 90% identity over an entire length of a nucleotide sequence to at least one of SEQ ID NO:1, SEQ ID NO:3 or SEQ ID NO:5, b) an immunogenic fragment of a nucleotide sequence having at least about 90% identity over at least 60% of the nucleotide sequence to at least one of SEQ ID NO:1, SEQ ID NO:3 or SEQ ID NO:5, c) a nucleotide sequence of SEQ ID NO:1, SEQ ID NO:3 or SEQ ID NO:5, or d) an immunogenic fragment of a nucleotide sequence of SEQ ID NO:1, SEQ ID NO:3 or SEQ ID NO:5.

In one embodiment, the nucleotide sequence encoding the peptide is operably linked to at least one regulatory sequence. In one embodiment, the regulatory sequence is at least one of a start codon, an IgE leader sequence or a stop codon.

In one embodiment, the nucleic acid molecule encodes a peptide comprising an amino acid sequence of at least one of a) an amino acid sequence having at least about 90% identity over an entire length of the amino acid sequence to at least one of SEQ ID NO:2, SEQ ID NO:4 or SEQ ID NO:6, b) an immunogenic fragment comprising at least about 90% identity over at least 60% of the amino acid sequence to at least one of SEQ ID NO:2, SEQ ID NO:4 or SEQ ID NO:6, c) the amino acid sequence of SEQ ID NO:2, SEQ ID NO:4 or SEQ ID NO:6, or d) an immunogenic fragment comprising at least 60% of the amino acid sequence of SEQ ID NO:2, SEQ ID NO:4 or SEQ ID NO:6, operably linked to an amino acid sequence as set forth in SEQ ID NO:7.

In one embodiment, the nucleic acid molecule comprises a nucleotide sequence of at least one of a) a nucleotide sequence having at least about 90% identity over an entire length of a nucleotide sequence to at least one of SEQ ID NO:1, SEQ ID NO:3 or SEQ ID NO:5, b) an immunogenic fragment of a nucleotide sequence having at least about 90% identity over at least 60% of the nucleotide sequence to at least one of SEQ ID NO:1, SEQ ID NO:3 or SEQ ID NO:5, c) a nucleotide sequence of SEQ ID NO:1, SEQ ID NO:3 or SEQ ID NO:5, or d) an immunogenic fragment of a nucleotide sequence of SEQ ID NO:1, SEQ ID NO:3 or SEQ ID NO:5, operably linked to an nucleotide sequence encoding SEQ ID NO:7.

In one embodiment, the nucleic acid molecule comprises an expression vector.

In one embodiment, the nucleic acid molecule is incorporated into a viral particle.

In one embodiment, the invention relates to an immunogenic composition comprising a peptide, wherein the peptide comprises an amino acid sequence of at least one of a) an amino acid sequence having at least about 90% identity over an entire length of the amino acid sequence to at least one of SEQ ID NO:2, SEQ ID NO:4 or SEQ ID NO:6, b) an immunogenic fragment comprising at least about 90% identity over at least 60% of the amino acid sequence to at least one of SEQ ID NO:2, SEQ ID NO:4 or SEQ ID NO:6, c) the amino acid sequence of SEQ ID NO:2, SEQ ID NO:4 or SEQ ID NO:6, or d) an immunogenic fragment comprising at least 60% of the amino acid sequence of SEQ ID NO:2, SEQ ID NO:4 or SEQ ID NO:6.

In one embodiment, the invention relates to a peptide, wherein the peptide comprises an amino acid sequence of at least one of a) an amino acid sequence having at least about 90% identity over an entire length of the amino acid sequence to at least one of SEQ ID NO:2, SEQ ID NO:4 or SEQ ID NO:6, b) an immunogenic fragment comprising at least about 90% identity over at least 60% of the amino acid sequence to at least one of SEQ ID NO:2, SEQ ID NO:4 or SEQ ID NO:6, c) the amino acid sequence of SEQ ID NO:2, SEQ ID NO:4 or SEQ ID NO:6, or d) an immunogenic fragment comprising at least 60% of the amino acid sequence of SEQ ID NO:2, SEQ ID NO:4 or SEQ ID NO:6.

In one embodiment, the invention relates to a method of inducing an immune response against a MCV T antigen in a subject in need thereof, the method comprising administering an immunogenic composition comprising a nucleic acid molecule encoding a modified Merkel Cell Polyomavirus (MCV) T antigen, wherein the T antigen comprises at least one mutation that disrupts at least one oncogenic feature of a native MCV T antigen, to the subject.

In one embodiment, the method of administering includes at least one of electroporation or injection.

In one embodiment, the invention relates to a method of treating or preventing a MCV associated pathology in subject in need thereof, the method comprising administering an immunogenic composition comprising a nucleic acid molecule encoding a modified Merkel Cell Polyomavirus (MCV) T antigen, wherein the T antigen comprises at least one mutation that disrupts at least one oncogenic feature of a native MCV T antigen, to the subject.

In one embodiment, the method of administering includes at least one of electroporation or injection.

In one embodiment, the MCV associated pathology is at least one of MCV infection or Merkel Cell Carcinoma.

BRIEF DESCRIPTION OF THE DRAWINGS

FIG. 1, comprising FIG. 1A through FIG. 1B, provides schematic diagrams of the LTAg and STAg.

FIG. 2, comprising FIG. 2A through FIG. 2B, provides schematic diagrams of the consensus LTAg and STAg.

FIG. 4, comprising FIG. 4A through FIG. 4B, provides exemplary experimental data demonstrating induction of an immune response following vaccination with LTAg and STAg alone or in combination.

FIG. 5, comprising FIG. 5A through FIG. 5B, provides exemplary experimental data characterizing the immunodominant epitopes for the LTAg and STAg.

FIG. 7, comprising FIG. 7A through FIG. 7F, provides exemplary experimental data demonstrating the levels of CD4$^+$ and CD8$^+$ T cell responses for cytokines following vaccination and stimulation for 5 hours with LTAg peptides.

FIG. 14, comprising FIG. 14A through FIG. 14F, provides exemplary experimental data demonstrating the levels of CD4$^+$ and CD8$^+$ T cell responses for cytokines following vaccination in CD-1 outbred mice and stimulation for 5 hours with LTAg peptides.

FIG. 15, comprising FIG. 15A through FIG. 15F, provides exemplary experimental data demonstrating the levels of CD4$^+$ and CD8$^+$ T cell responses for cytokines following vaccination in CD-1 outbred mice and stimulation for 5 hours with STAg peptides.

DETAILED DESCRIPTION

Figures 1A, 1B:
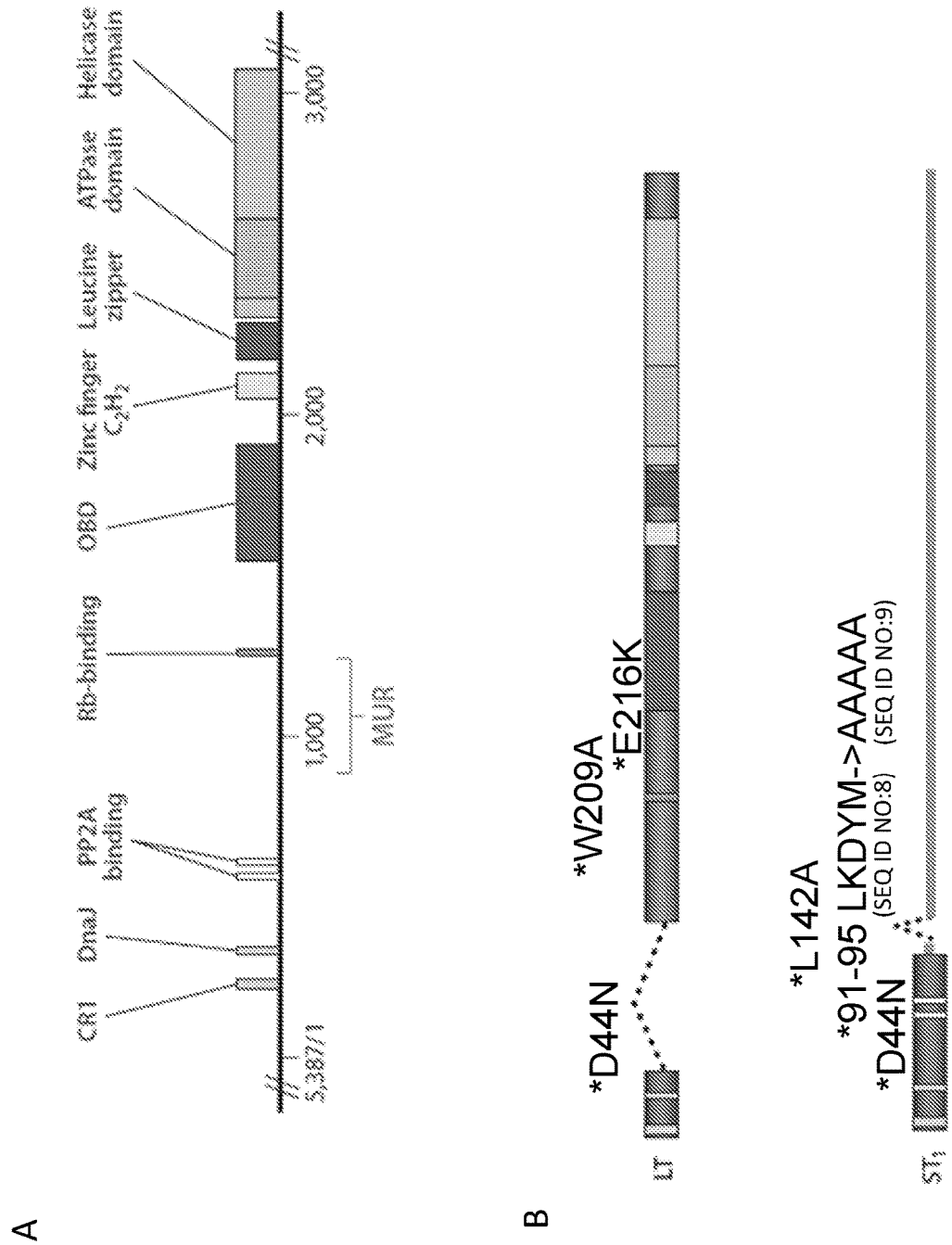
FIG. 1A depicts the oncogenic features of the LTAg and STAg.
FIG. 1B depicts that the design of the LTAg and STAg of the nucleic acid vaccine incorporate several mutations to disrupt the oncogenic features. *D44N-blocks binding to chaperone proteins; *W209A-blocks binding to hVam6p; *E216K-blocks binding to Rb and prevents transformation; *L142A-blocks binding to PP2A; *91-95LKDYM→AAAAA-blocks binding to Fbxw7 and prevents transformation.

Merkel Cell Polyomavirus (MCV) infection is associated with Merkel Cell Carcinoma (MCC), which currently has a 46% mortality rate.

In one embodiment, the invention includes a nucleic acid vaccine against MCV and MCC. In one embodiment, the vaccine comprise a plasmid encoding a consensus MCV T antigen. In one embodiment, the consensus MCV T antigen is a large T antigen (LTAg). In one embodiment, the consensus MCV T antigen is a small t antigen (STAg). In one embodiment, the consensus MCV T antigens further comprise mutations that disrupt the oncogenic features of native T antigens. As a vaccine candidate, an enhanced DNA (DNA)-based platform provides many advantages in genetic optimization and delivery techniques. As such, each MCV T antigen can be genetically-optimized, subcloned into modified mammalian expression vectors, and then delivered using in vivo electroporation (EP).

Vaccination in preclinical rodent studies was highly potent, as vaccination with synthetic consensus MCV T antigen constructs generates robust immune responses.

In some embodiments, the strategy employs a coding sequence for a synthetic consensus MCV T antigen. Coding sequence for a LTAg and a STAg are provided. In some embodiments, the strategy employs coding sequences for a single synthetic consensus MCV T antigen. In some embodiments, the strategy employs coding sequences for multiple synthetic consensus MCV T antigens.

As a candidate for vaccines, DNA vaccines exhibit a multitude of advantages including rapid and inexpensive up-scale production, stability at room temperature, and ease of transport, all of which further enhance this platform from an economic and geographic perspective. Due to the synthetic nature of the plasmids, antigen sequences can be quickly and easily modified in response to newly emergent strains and/or expanded to include additional vaccine components.

Optimization of plasmid DNA vectors and their encoded antigen genes have led to increases in in vivo immunogenicity. Cellular uptake and subsequent antigen expression are substantially amplified when highly-concentrated plasmid vaccine formulations are administered with in vivo electroporation, a technology that uses brief square-wave electric pulses within the vaccination site to drive plasmids into transiently permeabilized cells. In theory, a cocktail of DNA plasmids could be assembled for directing a highly-specialized immune response against any number of variable antigens. Immunity can be further directed by co-delivery with plasmid molecular adjuvants encoding species-specific cytokine genes as well as 'consensus-engineering' of the antigen amino acid sequences to help bias vaccine-induced immunity towards particular strains.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein may mean any molecule added to a nucleic acid vaccines to enhance antigenicity of the vaccine.

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes a protein. The coding sequence may further include initiation and termination signals operably linked to regulatory elements including a promoter and polyadenylation signal capable of directing expression in the cells of an individual or mammal to whom the nucleic acid is administered. The coding sequence may optionally further comprise a start codon that encodes an N terminal methionine or a signal peptide such as an IgE or IgG signal peptide.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Consensus" or "consensus sequence" as used herein may mean a synthetic nucleotide sequence, or corresponding polypeptide sequence, constructed based on analysis of an alignment of multiple sequences (e.g., multiple sequences of a particular virus antigen.)

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a percentage of a full length polypeptide sequence or nucleotide sequence. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the full length of the parental nucleotide sequence or amino acid sequence or variant thereof.

"Genetic construct" as used herein refers to the DNA or RNA molecules that comprise a nucleotide sequence which encodes a protein, such as an antibody. The genetic construct may also refer to a DNA molecule which transcribes an RNA. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more consensus antigen via the provided vaccines. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid molecule (e.g., probe) will hybridize to a second nucleic acid molecule (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Treatment" or "treating," as used herein can mean protecting a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" as used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleotide sequence that is substantially identical over the full length of the full gene sequence or a fragment thereof. The nucleotide sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid molecule containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Description

The invention provides an optimized consensus sequence encoding a MCV T antigen. In one embodiment, the MCV T antigen encoded by the optimized consensus sequence is capable of eliciting an immune response in a mammal. In one embodiment, the MCV T antigen encoded by the optimized consensus sequence can comprise an epitope(s) that makes it particularly effective as an immunogen against which an immune response can be induced.

The optimized consensus sequence can be a consensus sequence derived from two or more MCV T antigens. The optimized consensus sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The MCV T antigen encoded by the optimized consensus sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The antigen encoded by the optimized consensus sequence can be designed to elicit stronger cellular and/or humoral immune responses than a corresponding non-optimized antigen.

Provided herein are MCV T antigens that can be used to induce immunity against MCV in genetically diverse subjects with MCV infection. In one embodiment, the present invention provides an immunogenic composition comprising one or more nucleic acid molecules that are capable of generating in a mammal an immune response against a MCV T antigen. The present invention also provides isolated nucleic acid molecules that are capable of generating in a mammal an immune response against a MCV T antigen. In one embodiment, the nucleic acid molecule comprises an optimized nucleotide sequence encoding a consensus MCV T antigen.

In one embodiment, the MCV T antigens are modified to reduce or disrupt at least one oncogenic feature of a native MCV T antigen. In various embodiments, the MCV T antigens are modified to reduce or disrupt at least one of CR1 binding, DnaJ binding, phophatase pp2A-binding binding, Rb binding, ATPase activity, helicase activity, chaperone protein binding, hVam6p binding, Fbxw7 binding, origin binding, and transformation. In one embodiment, the MCV T antigen comprises at least one mutation at D44, W209, E216, L142, L91, K92, D93, Y94 or M95 relative to the native T antigen sequence. In one embodiment, the MCV T antigen comprises at least one of a D44N mutation, a W209A, an E216K mutation, an L142A mutation, an L91A mutation, a K92A mutation, a D93A mutation, a Y94A mutation and a M95A mutation. In one embodiment, the MCV LTAg comprises at least one of a D44N mutation, a W209A, and an E216K mutation. In one embodiment, the MCV LTAg comprises a D44N mutation, a W209A, and an E216K mutation. In one embodiment, the MCV STAg comprises at least one of a D44N mutation, an L142A mutation, an L91A mutation, a K92A mutation, a D93A mutation, a Y94A mutation and a M95A mutation. In one embodiment, the MCV STAg comprises a D44N mutation, an L142A mutation, an L91A mutation, a K92A mutation, a D93A mutation, a Y94A mutation and a M95A mutation.

Consensus amino acid sequences for MCV T antigens include SEQ ID NO:2, SEQ ID NO:4, and variants thereof and fragments of SEQ ID NO:2, SEQ ID NO:4, and variants thereof An exemplary amino acid sequence of a modified synthetic consensus MCV LTAg is provided as SEQ ID NO:2. An exemplary amino acid sequence of a modified synthetic consensus MCV STAg is provided as SEQ ID NO:2.

In one embodiment, the invention provides compositions comprising a nucleic acid molecule comprising a nucleotide sequence that encodes a modified synthetic consensus MCV T antigen. In one embodiment, a nucleotide sequence which encodes a modified synthetic consensus MCV LTAg is provided as SEQ ID NO:1, which encodes SEQ ID NO:2. In one embodiment, a nucleotide sequence which encodes a modified synthetic consensus MCV STAg is provided as SEQ ID NO:3, which encodes SEQ ID NO:4.

In various embodiments, the invention provides compositions comprising a combination of a modified LTAg and a modified STAg, or one or more nucleic acid molecules encoding the same. The compositions may comprise a plurality of copies of a single nucleic acid molecule such a single plasmid, or a plurality of copies of two or more different nucleic acid molecules such as two or more different plasmids.

Compositions may comprise a single nucleic acid molecule, such as a plasmid, that contains coding sequence for multiple consensus MCV T antigens. In one embodiment, the compositions may comprise a single nucleic acid molecule comprising nucleotide sequences that encode a MCV LTAg and a MCV STAg. In one embodiment, each coding sequence for each consensus MCV T antigen is on a separate plasmid.

Accordingly, compositions that comprise one or more nucleotide sequence that encode multiple consensus MCV T antigens may be on a single plasmid. In one embodiment, a composition comprises a single plasmid that encodes a MCV LTAg and a MCV STAg under a single promoter. In such an embodiment, the sequence that encodes the MCV LTAg and the sequence that encodes the MCV STAg may be linked by a fusion peptide sequence, for example a furin cleavage sequence. An exemplary amino acid sequence of a single construct comprising a modified synthetic consensus MCV LTAg and MCV STAg linked by a furin cleavage site is provided as SEQ ID NO:6. In one embodiment, a single nucleotide sequence which encodes a modified synthetic consensus MCV LTAg and MCV STAg linked by a furin cleavage sequence is provided as SEQ ID NO:5, which encodes SEQ ID NO:6.

In one embodiment, an optimized consensus encoded MCV T antigen is operably linked to one or more regulatory elements. In one embodiment, a regulatory element is a leader sequence. In one embodiment, the leader sequence is an IgE leader sequence. In one embodiment, the IgE leader sequence has an amino acid sequence as set forth in SEQ ID NO:7. Therefore in one embodiment, the invention relates to an amino acid sequence as set forth in SEQ ID NO:2, SEQ ID NO:4 or SEQ ID NO:6 operably linked to an amino acid sequence as set forth in SEQ ID NO:7. In one embodiment, the invention relates to a nucleotide sequence encoding an amino acid sequence as set forth in SEQ ID NO:2, SEQ ID NO:4 or SEQ ID NO:6 operably linked to an amino acid sequence as set forth in SEQ ID NO:7.

In one embodiment, a regulatory element is a start codon. Therefore, in one embodiment, the invention relates to a nucleotide sequence as set forth in SEQ ID NO:1, SEQ ID NO:3 or SEQ ID NO:5, or a fragment or homolog thereof, operably linked to a nucleotide sequence comprising a start codon at the 5' terminus. In one embodiment, the invention relates to an amino acid sequence as set forth in SEQ ID NO:2, SEQ ID NO:4 or SEQ ID NO:6 or a fragment or homolog thereof, operably linked to an amino acid encoded by a start codon (e.g., a Methionine) at the N-terminus.

In one embodiment, a regulatory element is at least one stop codon. Therefore, in one embodiment, the invention relates to a nucleotide sequence as set forth in SEQ ID NO:1, SEQ ID NO:3 or SEQ ID NO:5, or a fragment or homolog thereof, operably linked to a nucleotide sequence comprising at least one stop codon at the 3' terminus. In one embodiment, the nucleotide sequence is operably linked to two stop codons to increase the efficiency of translational termination.

In one embodiment, nucleic acid molecule can encode a peptide having the amino acid sequence set forth in SEQ ID NO:2, SEQ ID NO:4 or SEQ ID NO:6. In one embodiment, the nucleic acid molecule comprises the nucleotide sequence set forth in SEQ ID NO:1, SEQ ID NO:3 or SEQ ID NO:5. In some embodiments, the sequence can be the nucleotide sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO:1, SEQ ID NO:3 or SEQ ID NO:5. In other embodiments, sequence can be the nucleotide sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2, SEQ ID NO:4 or SEQ ID NO:6.

In some embodiments, the nucleic acid molecule comprises an RNA sequence that is a transcript from a DNA sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleotide sequence set forth in SEQ ID NO:1, SEQ ID NO:3 or SEQ ID NO:5. In some embodiments, the nucleic acid molecule comprises an RNA sequence that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the amino acid sequence set forth in SEQ ID NO:2, SEQ ID NO:4 or SEQ ID NO:6.

In some embodiments, the nucleic acid molecule may comprise a nucleotide sequence that encodes a full length consensus MCV T antigen. The nucleic acid molecules may comprise a sequence that encodes SEQ ID NO:2, SEQ ID NO:4 or SEQ ID NO:6. The nucleic acid molecules may comprise a nucleotide sequence of SEQ ID NO:1, SEQ ID NO:3 or SEQ ID NO:5. The nucleic acid molecule may optionally comprise coding sequences that encode a signal peptide such as for example an IgE or IgG signal peptide.

The consensus-MCV T antigen can be a peptide having the amino acid sequence set forth in SEQ ID NO:2, SEQ ID NO:4 or SEQ ID NO:6. In some embodiments, the antigen can have an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2, SEQ ID NO:4 or SEQ ID NO:6.

Immunogenic fragments of SEQ ID NO:2, SEQ ID NO:4 or SEQ ID NO:6 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of the full length of SEQ ID NO:2, SEQ ID NO:4 or SEQ ID NO:6. In some embodiments, immunogenic fragments include a leader sequence, such as for example an immunoglobulin leader, such as the IgE leader. In some embodiments, immunogenic fragments are free of a leader sequence.

Immunogenic fragments of proteins with amino acid sequences homologous to immunogenic fragments of SEQ ID NO:2, SEQ ID NO:4 or SEQ ID NO:6, can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2, SEQ ID NO:4 or SEQ ID NO:6. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

In one embodiment, an immunogenic fragment of a nucleic acid molecule encodes at least one immunodominant or sub-immunodominant epitope of a full length optimized consensus MCV T antigen.

Some embodiments relate to immunogenic fragments of SEQ ID NO:1, SEQ ID NO:3 or SEQ ID NO:5 comprising at least 60%, at least 65%, at least 70%, at least 75%, at least 80%, at least 85%, at least 90%, at least 95%, at least 96%, at least 97%, at least 98% or at least 99% of the full length of SEQ ID NO:1, SEQ ID NO:3 or SEQ ID NO:5. Immunogenic fragments can be at least 96%, at least 97% at least 98% or at least 99% homologous to fragments of SEQ ID NO:1, SEQ ID NO:3 or SEQ ID NO:5. In some embodiments, immunogenic fragments include sequences that encode a leader sequence, such as for example an immunoglobulin leader, such as the IgE leader. In some embodiments, fragments are free of coding sequences that encode a leader sequence.

In one embodiment, the nucleic acid molecule comprises a sequence at least 90% homologous to SEQ ID NO:1, SEQ ID NO:3 or SEQ ID NO:5.

In one embodiment, the nucleic acid molecule comprises an RNA sequence encoding a consensus MCV T antigen sequence described herein. For example, nucleic acids may comprise an RNA sequence encoding one or more of SEQ ID NO:2, SEQ ID NO:4 or SEQ ID NO:6, a variant thereof, a fragment thereof or any combination thereof.

In some embodiments, the nucleic acid molecule includes a sequence that encodes for a MCV T antigen minus an IgE leader sequence on the N-terminal end of the coding sequence. In some embodiments, the DNA nucleic acid molecule further comprises an IgE leader sequence attached to an N-terminal end of the coding sequence and operably linked to the promoter.

The nucleic acid molecule can further include a polyadenylation sequence attached to the C-terminal end of the coding sequence. In one embodiment, the nucleic acid molecule is codon optimized.

Vaccines and Immunogenic Compositions

Immunogenic compositions, such as vaccines, are provided comprising an optimized consensus sequence, an optimized consensus-encoded antigen, a fragment thereof, a variant thereof, or a combination thereof. The immunogenic composition can significantly induce an immune response of a subject administered with the immunogenic composition against the MCV T antigen. The vaccine may comprise a plurality of the nucleic acid molecules, or combinations thereof. The vaccine may be provided to induce a therapeutic or prophylactic immune response.

The immunogenic composition can be a DNA vaccine, an RNA vaccine, a peptide vaccine, or a combination vaccine. The vaccine can include an optimized consensus nucleotide sequence encoding an antigen. The nucleotide sequence can be DNA, RNA, cDNA, a variant thereof, a fragment thereof, or a combination thereof. The nucleotide sequence can also include additional sequences that encode linker, leader, or tag sequences that are linked to the antigen by a peptide bond. The peptide vaccine can include an antigen, a variant thereof, a fragment thereof, or a combination thereof. The combination DNA and peptide vaccine can include the above described optimized consensus nucleotide sequence and the encoded antigen.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the one or more MCV T antigens. The RNA vaccine can be introduced into the cell.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing protective T cell responses; and providing ease of administration, few side effects, biological stability, and low cost per dose.

Provided herein is an immunogenic composition capable of generating in a mammal an immune response against MCV. The immunogenic composition may comprise each plasmid as discussed above. The immunogenic composition may comprise a plurality of the plasmids, or combinations thereof. The immunogenic composition may be provided to induce a therapeutic or prophylactic immune response.

Immunogenic compositions may be used to deliver nucleic acid molecules that encode one or more consensus MCV T antigen. Immunogenic compositions are preferably compositions comprising plasmids.

The immunogenic composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the immunogenic composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the immunogenic compositions may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the immunogenic composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the immunogenic composition. The one or more adjuvants may be proteins and/or nucleic acid molecules that encode proteins selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or a combination thereof.

In some embodiments, the adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/US10/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

The immunogenic composition may further comprise a genetic vaccine facilitator agent as described in U.S. Ser. No. 021,579 filed Apr. 1, 1994, which is fully incorporated by reference.

The immunogenic composition may comprise the consensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of a nucleic acid molecule of the invention. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of a nucleic acid molecule of the invention. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of a nucleic acid molecule of the invention.

In other embodiments, the pharmaceutical composition can comprise up to and including 15, 20, 25, 30, 35, 40, 45, 50, 55, 60, 65, 70, 75, 80, 85, 90, 95 or 100 nanograms of a nucleic acid molecule of the invention. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of a nucleic acid molecule of the invention. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of a nucleic acid molecule of the invention.

The immunogenic composition may be formulated according to the mode of administration to be used. An injectable immunogenic composition pharmaceutical composition may be sterile, pyrogen free and particulate free. An isotonic formulation or solution may be used. Additives for isotonicity may include sodium chloride, dextrose, mannitol, sorbitol, and lactose. The immunogenic composition may comprise a vasoconstriction agent. The isotonic solutions may include phosphate buffered saline. Immunogenic composition may further comprise stabilizers including gelatin and albumin. The stabilizing may allow the formulation to be stable at room or ambient temperature for extended periods of time such as LGS or polycations or polyanions to the immunogenic composition formulation.

The immunogenic composition may be stable at room temperature (25° C.) for more than 1 week, in some embodiments for more than 2 weeks, in some embodiments for more than 3 weeks, in some embodiments for more than 4 weeks, in some embodiments for more than 5 weeks, and in some embodiments for more than 6 weeks. In some embodiments, the vaccine is stable for more than one month, more than 2 months, more than 3 months, more than 4 months, more than 5 months, more than 6 months, more than 7 months, more than 8 months, more than 9 months, more than 10 months, more than 11 months, or more than 12 months. In some embodiments, the vaccine is stable for more than 1 year, more than 2 years, more than years, or more than 5 years. In one embodiment, the immunogenic composition is stable under refrigeration (2-8° C.). Accordingly, in one embodiment, the immunogenic composition does not require frozen cold-chain. An immunogenic composition is stable if it retains its biological activity for a sufficient period to allow its intended use (e.g., to generate an immune response in a subject). For example, for immunogenic compositions that are to be stored, shipped, etc., it may be desired that the immunogenic compositions remain stable for months to years.

Immune Response

The immunogenic composition can induce an immune response in the subject administered the composition. The induced immune response can be specific for a MCV T antigen. The induced immune response can be reactive with a MCV T antigen related to the optimized consensus-encoded antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized consensus-encoded antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized consensus nucleotide sequences disclosed herein.

The immunogenic composition can induce a humoral immune response in the subject administered the immunogenic composition. The induced humoral immune response can be specific for a MCV T antigen. The induced humoral immune response can be reactive with the MCV T antigen related to the optimized consensus-encoded antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized MCV T antigen.

The humoral immune response induced by the immunogenic composition can include an increased level of IgG antibodies associated with the subject administered the immunogenic composition as compared to a subject not administered the immunogenic composition. These IgG antibodies can be specific for the MCV T antigen genetically related to the optimized consensus antigen. These IgG antibodies can be reactive with the MCV T antigen genetically related to the optimized consensus antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized MCV T antigen.

The immunogenic composition can induce a cellular immune response in the subject administered the immunogenic composition. The induced cellular immune response can be specific for a MCV T antigen related to the optimized consensus-encoded antigen. The induced cellular immune response can be reactive to the MCV T antigen related to the optimized consensus-encoded antigen. The induced cellular immune response can include eliciting a $CD8^+$ T cell response. The elicited $CD8^+$ T cell response can be reactive with the MCV T antigen genetically related to the optimized consensus antigen. The elicited $CD8^+$ T cell response can be polyfunctional. The induced cellular immune response can include eliciting a $CD8^+$ T cell response, in which the $CD8^+$ T cells produce interferon-gamma (IFN-γ), tumor necrosis factor alpha (TNF-α), interleukin-2 (IL-2), or a combination of IFN-γ and TNF-α.

The induced cellular immune response can include an increased $CD8^+$ T cell response associated with the subject administered the immunogenic composition as compared to the subject not administered the immunogenic composition. The $CD8^+$ T cell response associated with the subject administered the immunogenic composition can be increased by about 2-fold to about 30-fold, about 3-fold to about 25-fold, or about 4-fold to about 20-fold as compared to the subject not administered the immunogenic composition. The CD8+ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition or a subject administered a non-optimized MCV T antigen.

The induced cellular immune response can include an increased frequency of CD107a/IFNγ/T-bet triple-positive CD8 T cells that are reactive against the MCV T antigen. The frequency of CD107a/IFNγ/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized MCV T antigen.

The induced cellular immune response can include an increased frequency of CD107a/IFNγ double-positive CD8 T cells that are reactive against the MCV T antigen. The frequency of CD107a/IFNγ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition or a subject administered a non-optimized MCV T antigen.

The cellular immune response induced by the immunogenic composition can include eliciting a CD4+ T cell response. The elicited CD4+ T cell response can be reactive with the MCV T antigen genetically related to the optimized consensus antigen. The elicited CD4+ T cell response can be polyfunctional. The induced cellular immune response can include eliciting a CD4+ T cell response, in which the CD4+ T cells produce IFN-γ, TNF-α, IL-2, or a combination of IFN-γ and TNF-α.

The induced cellular immune response can include an increased frequency of CD4+ T cells that produce IFN-γ. The frequency of CD4+IFN-γ+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized MCV T antigen.

The induced cellular immune response can include an increased frequency of CD4+ T cells that produce TNF-α. The frequency of CD4+ TNF-α+ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition or a subject administered a non-optimized MCV T antigen.

The induced cellular immune response can include an increased frequency of CD4+ T cells that produce both IFN-γ and TNF-α. The frequency of CD4+IFN-γ+TNF-α+ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition or a subject administered a non-optimized MCV T antigen.

The immunogenic composition can further induce an immune response when administered to different tissues such as the muscle or skin. The immunogenic composition can further induce an immune response when administered via electroporation, or injection, or subcutaneously, or intramuscularly.

Vector

The nucleotide construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid construct may be chimeric, meaning that at least one of its components is heterologous with respect to at least one of its other components.

(2) Plasmid

The one or more vectors can be a plasmid. The plasmid may be useful for transfecting cells with the recombinant nucleic acid construct. The plasmid may be useful for introducing the recombinant nucleic acid construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NO:1, SEQ ID NO:3 or SEQ ID NO:5, or a variant thereof or a fragment thereof. In another embodiment, the nucleotide sequence comprises an RNA sequence transcribed by a DNA sequence encoding a polypeptide sequence at least 90% homologous to one of SEQ ID NO:2, SEQ ID NO:4 or SEQ ID NO:6 or a variant thereof or a fragment thereof. Accordingly, in one embodiment, the invention provides an RNA molecule encoding one or more of the MCV T antigens. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(4) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid construct. The LEC may be any linear DNA devoid of any phosphate backbone. The LEC may not contain any antibiotic resistance genes and/or a phosphate backbone. The LEC may not contain other nucleotide sequences unrelated to the desired gene expression.

The LEC may be derived from any plasmid capable of being linearized. The plasmid may be capable of expressing the heavy chain polypeptide and/or light chain polypeptide encoded by the recombinant nucleic acid construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid construct.

The LEC can be perM2. The LEC can be perNP. perNP and perMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(6) Method of Preparing the Vector

Provided herein is a method for preparing the one or more vectors in which the recombinant nucleic acid construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

Multiple Vectors

The immunogenic composition may comprise a plurality of copies of a single nucleic acid molecule such a single plasmid, or a plurality of copies of two or more different nucleic acid molecules such as two or more different plasmids. For example an immunogenic composition may comprise plurality of two, three, four, five, six, seven, eight, nine or ten or more different nucleic acid molecules. Such compositions may comprise plurality of two, three, four, five, six, or more different plasmids.

Immunogenic compositions may comprise nucleic acid molecules, such as plasmids, that collectively contain coding sequence for a MCV T antigen. Immunogenic compositions may comprise nucleic acid molecules, such as plasmids, that collectively contain coding sequence for multiple antigens. In one embodiment, the antigens are a MCV T antigen and one or more additional cancer antigen. Immunogenic compositions may comprise nucleic acid molecules, such as plasmids, that collectively contain coding sequence for one or more MCV T antigen and one or more cancer antigen.

Cancer Antigens

The immunogenic composition can comprise one or more cancer antigens such as WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ML-IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGS5, SART3, STn, Carbonic anhydrase 1×, PAXS, OV-TES1, Sperm Protein 17, LCK, HMWMAA, Sperm fibrous sheath proteins, AKAP-4, SSX2, XAGE 1, B7H3, Legumain, Tie 2, Page4, VEGFR2, MAD-CT-1 (protamine 2), MAD-CT-2, and FOS-related antigen 1 to treat or prevent a tumor associated pathology. The immunogenic composition can further combine one or more cancer antigens WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase 3 (PR1), Bcr-abl, Tyrosinase, Survivin, PSA, hTERT, EphA2, PAP, ML-IAP, AFP, EpCAM, ERG, NA17, PAX3, ALK, Androgen Receptor, Cyclin B1, Polysialic Acid, MYCN, TRP-2, RhoC, GD3, Fucosyl GM1, Mesothelin, PSCA, MAGE A1, sLe(a), CYP1B1, PLAC1, GM3 ganglioside, BORIS, Tn, GloboH, ETV6-AML, NY-BR-1, RGS5, SART3, STn, Carbonic anhydrase IX, PAXS, OY-TES1, Sperm Protein 17, LCK, HMWMAA, Sperm fibrous sheath proteins, AKAP-4, SSX2, XAGE 1, B7H3, Legumain, Tie 2, Page4, VEGFR2, MAD-CT-1 (protamine 2), MAD-CT-2, and FOS-related antigen with an optimized consensus encoded MCV T antigen for treating or preventing a tumor associated pathology. Other combinations of cancer antigens may also be applied for treating or preventing a tumor associated pathology.

Methods

Provided herein are methods of treating, protecting against, and/or preventing a MCV associated disease in a subject in need thereof by administering one or more immunogenic composition described herein to the subject. Administration of the immunogenic composition to the subject can induce or elicit an immune response in the subject. The induced immune response can be used to treat, prevent, and/or protect against disease, for example, MCV infection or MCC associated with MCV infection.

Provided herein is a method for delivering the immunogenic composition for providing genetic constructs and proteins of the consensus antigen which comprise epitopes that make them particular effective against MCV or MCC, against which an immune response can be induced. The method of delivering the immunogenic composition or vaccination may be provided to induce a therapeutic and prophylactic immune response. The vaccination process may generate in the mammal an immune response against MCV or MCC. The immunogenic composition may be delivered to an individual to modulate the activity of the mammal's immune system and enhance the immune response. The delivery of the immunogenic composition may be the transfection of the consensus antigen as a nucleic acid molecule that is expressed in the cell and delivered to the surface of the cell upon which the immune system recognized and induces a cellular, humoral, or cellular and humoral response. The delivery of the immunogenic composition may be used to induce or elicit and immune response in mammals against MCV or MCC by administering to the mammals the immunogenic composition as discussed above.

Upon delivery of the immunogenic composition and plasmid into the cells of the mammal, the transfected cells will express and secrete consensus antigens for each of the plasmids injected from the immunogenic composition. These proteins will be recognized as foreign by the immune system and antibodies will be made against them. These antibodies will be maintained by the immune system and allow for an effective response to subsequent infections by MCV.

The immunogenic composition may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

The induced immune response can include an induced humoral immune response and/or an induced cellular immune response. The humoral immune response can be induced by about 1.5-fold to about 16-fold, about 2-fold to about 12-fold, or about 3-fold to about 10-fold. The induced cellular immune response can include a $CD8^+$ T cell response, which is induced by about 2-fold to about 30-fold, about 3-fold to about 25-fold, or about 4-fold to about 20-fold.

The immunogenic composition dose can be between 1 μg to 10 mg active component/kg body weight/time, and can be 20 μg to 10 mg component/kg body weight/time. The immunogenic composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of immunogenic composition doses for effective treatment can be 1, 2, 3, 4, 5, 6, 7, 8, 9, or 10.

The immunogenic composition can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration.

The immunogenic composition can be administered prophylactically or therapeutically. In prophylactic administration, the immunogenic compositions can be administered in an amount sufficient to induce an immune response. In therapeutic applications, the immunogenic compositions are administered to a subject in need thereof in an amount sufficient to elicit a therapeutic effect. An amount adequate to accomplish this is defined as "therapeutically effective dose." Amounts effective for this use will depend on, e.g., the particular composition of the immunogenic composition regimen administered, the manner of administration, the stage and severity of the disease, the general state of health of the subject, and the judgment of the prescribing physician.

The immunogenic composition can be administered by methods well known in the art as described in Donnelly et al. (Ann. Rev. Immunol. 15:617-648 (1997)); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the immunogenic composition can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The immunogenic composition can be delivered via a variety of routes. Typical delivery routes include parenteral administration, e.g., intradermal, intramuscular or subcutaneous delivery. Other routes include oral administration, intranasal, and intravaginal routes. For the DNA of the immunogenic composition in particular, the immunogenic composition can be delivered to the interstitial spaces of tissues of an individual (Feigner et al., U.S. Pat. Nos. 5,580,859 and 5,703,055, the contents of all of which are incorporated herein by reference in their entirety). The immunogenic composition can also be administered to muscle, or can be administered via intradermal or subcutaneous injections, or transdermally, such as by iontophoresis. Epidermal administration of the immunogenic composition can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The immunogenic composition can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the immunogenic composition.

The immunogenic composition can be a liquid preparation such as a suspension, syrup or elixir. The immunogenic composition can also be a preparation for parenteral, subcutaneous, intradermal, intramuscular or intravenous administration (e.g., injectable administration), such as a sterile suspension or emulsion.

The immunogenic composition can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

Method of Cancer Treatment with the Vaccine

The vaccine can be used to generate or elicit an immune response in a mammal that is reactive or directed to a cancer or tumor (e.g., MCC) of the mammal or subject in need thereof. The elicited immune response can prevent cancer or tumor growth.

The elicited immune response can prevent and/or reduce metastasis of cancerous or tumor cells. Accordingly, the vaccine can be used in a method that treats and/or prevents cancer or tumors in the mammal or subject administered the vaccine.

In some embodiments, the administered vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as CD8+ (CTL) to attack and kill tumor cells; (3) increase T helper cell responses; (4) and increase inflammatory responses via IFN-γ and TFN-α or preferably all of the aforementioned.

In some embodiments, the immune response can generate a humoral immune response and/or an antigen-specific cytotoxic T lymphocyte (CTL) response that does not cause damage to or inflammation of various tissues or systems (e.g., brain or neurological system, etc.) in the subject administered the vaccine.

In some embodiments, the administered vaccine can increase tumor free survival, reduce tumor mass, increase tumor survival, or a combination thereof in the subject. The administered vaccine can increase tumor free survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% or more in the subject. The administered vaccine can reduce tumor mass by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% or more in the subject after immunization. The administered vaccine can prevent and block increases in monocyte chemoattractant protein 1 (MCP-1), a cytokine secreted by myeloid derived suppressor cells, in the subject. In some embodiments, the administered vaccine can prevent and block increases in MCP-1 within the cancerous or tumor tissue in the subject, thereby reducing vascularization of the cancerous or tumor tissue in the subject.

The administered vaccine can increase tumor survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% or more in the subject. In some embodiments, the vaccine can be administered to the periphery (as described in more detail below) to establish an antigen-specific immune response targeting the cancerous or tumor cells or tissue to clear or eliminate the cancer or tumor expressing the one or more MCV T antigens without damaging or causing illness or death in the subject administered the vaccine.

The administered vaccine can increase a cellular immune response in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase the cellular immune response in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The administered vaccine can increase interferon gamma (IFN-γ) levels in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase IFN-γ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The vaccine dose can be between 1 μg to 10 mg active component/kg body weight/time and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

Combinational Therapies with Checkpoint Inhibitors

The present invention is also directed to a method of increasing an immune response in a mammal using the vaccine as described above in combination with one or more checkpoint inhibitor. In one embodiment, the vaccine as described above can comprise the MCV T antigen and an antibody to a checkpoint protein. "Checkpoint inhibitor" as used herein includes inhibitors or molecules that block immune checkpoints as commonly understood in the field of cancer immunotherapy. More commonly the checkpoint inhibitors are antibodies that block the immune checkpoint proteins. Immune checkpoint proteins include, but are not limited to, PD1, PDL1, PDL2, CTLA-4, LAG3, TIM3, B7-H3, BTLA, VISTA, CD40, CEACAM1, CD80, CD86, OX40, CD27, GITR, DNAM-1, TIGIT, TMIGD2 and DC-SIGN. Some examples of known checkpoint inhibitors include, but are not limited to, ipilimumab, pembrolizumab, nivolumab, pidilizumab, avelumab and others.

The combination can be in a single formulation or can be separate and administered in sequence (either MCV T antigen first and then checkpoint inhibitor, or checkpoint inhibitor first and then MCV T antigen). In some embodiments, the MCV T antigen can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the checkpoint inhibitor is administered to the subject. In other embodiments, the checkpoint inhibitor can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the MCV T antigen is administered to the subject.

The combination of the MCV T antigen and checkpoint inhibitor induces the immune system more efficiently than a vaccine comprising the MCV T antigen alone. This more efficient immune response provides increased efficacy in the treatment and/or prevention of a particular cancer.

In some embodiments, the immune response can be increased by about 0.5-fold to about 15-fold, about 0.5-fold to about 10-fold, or about 0.5-fold to about 8-fold. Alternatively, the immune response in the subject administered the vaccine can be increased by at least about 0.5-fold, at least about 1.0-fold, at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, or at least about 15.0-fold.

In still other alternative embodiments, the immune response in the subject administered the vaccine can be increased about 50% to about 1500%, about 50% to about 1000%, or about 50% to about 800%. In other embodiments, the immune response in the subject administered the vaccine can be increased by at least about 50%, at least about 100%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, at least about 1200%, at least about 1250%, at least about 1300%, at least about 1350%, at least about 1450%, or at least about 1500%.

The vaccine dose can be between 1 µg to 10 mg active component/kg body weight/time, and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

Merkel Cell Carcinoma

The vaccine can be used to generate or elicit an immune response in a mammal that is reactive or directed to a Merkel Cell Carcinoma (MCC) in the mammal or subject in need thereof. The elicited immune response can prevent MCC growth. The elicited immune response can reduce MCC growth. The elicited immune response can prevent and/or reduce metastasis of cancerous or tumor cells from a MCC. Accordingly, the vaccine can be used in a method that treats and/or prevents MCC in the mammal or subject administered the vaccine.

In some embodiments, the administered vaccine can mediate clearance or prevent growth of MCC by inducing (1) humoral immunity via B cell responses to generate antibodies that target an MCV T antigen expressed by MCC cells; (2) increase cytotoxic T lymphocyte such as CD8+ (CTL) to attack and kill MCC cells; (3) increase T helper cell responses; and (4) increase inflammatory responses via IFN-γ and TFN-α or all of the aforementioned.

In some embodiments, the administered vaccine can increase MCC free survival, reduce MCC mass, increase MCC survival, or a combination thereof in the subject. The administered vaccine can increase MCC free survival by 30%, 31%, 32%, 33%, 34%, 35%, 36%, 37%, 38%, 39%, 40%, 41%, 42%, 43%, 44%, and 45% or more in the subject. The administered vaccine can reduce MCC mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% or more in the subject after immunization. The administered vaccine can prevent and block increases in monocyte chemoattractant protein 1 (MCP-1), a cytokine secreted by myeloid derived suppressor cells, in the subject. In some embodiments, the administered vaccine can prevent and block increases in MCP-1 within the MCC tissue in the subject, thereby reducing vascularization of the MCC tissue in the subject. The administered vaccine can increase MCC survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% or more in the subject.

Combination Treatments

The immunogenic composition may be administered in combination with other proteins and/or genes encoding CCL20, α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, MHC, CD80, CD86, IL-28, IL-1, IL-2, IL-4, IL-5, IL-6, IL-10, IL-18, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. In some embodiments, the immunogenic composition is administered in combination with one or more of the following nucleic acid molecules and/or proteins: nucleic acid molecules selected from the group consisting of nucleic acid molecules comprising coding sequence that encode one or more of CCL20, IL-12, IL-15, IL-28, CTACK, TECK, MEC and RANTES or functional fragments thereof, and proteins selected from the group consisting of: CCL02, IL-12 protein, IL-15 protein, IL-28 protein, CTACK protein, TECK protein, MEC protein or RANTES protein or functional fragments thereof.

The immunogenic composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The immunogenic composition may be administered by traditional syringes, needleless injection devices, "microprojectile bombardment gone guns", or other physical methods such as electroporation ("EP"), "hydrodynamic method", or ultrasound.

The plasmid of the immunogenic composition may be delivered to the mammal by several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The consensus antigen may be delivered via DNA injection and along with in vivo electroporation.

Electroporation

Administration of the immunogenic composition via electroporation may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, Pa.) or Elgen electroporator (Inovio Pharmaceuticals, Plymouth Meeting, Pa.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the immunogenic compositions of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the immunogenic compositions include those provided in co-pending and co-owned U.S. patent application Ser. No. 11/874,072, filed Oct. 17, 2007, which claims the benefit under 35 USC 119(e) to U.S. Provisional application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

Generation of Antigens In Vitro and Ex Vivo

In one embodiment, the optimized consensus MCV T antigen is generated in vitro or ex vivo. For example, in one embodiment, a nucleic acid encoding an optimized consensus MCV T antigen can be introduced and expressed in an in vitro or ex vivo cell.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

EXAMPLES

The present invention is further illustrated in the following Example. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: Nucleic Acid Vaccine Targeting Merkel Cell Polyomavirus

Figure 2A:
FIG. 2A depicts a diagram of the consensus sequence of the LTAg designed from all available NCBI LTAg sequences.
Figure 2B:
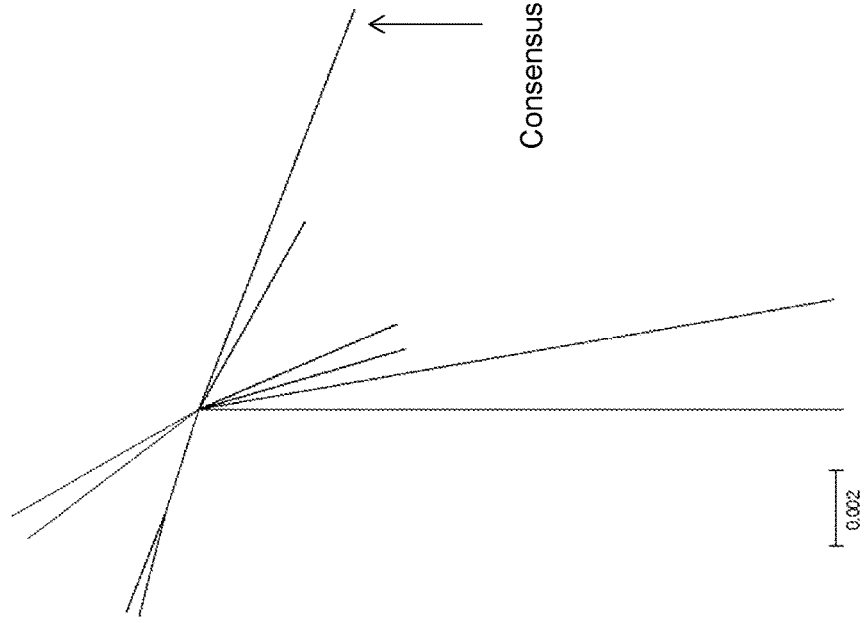
FIG. 2B depicts a diagram of the consensus sequence of the STAg designed from all available NCBI STAg sequences. These antigen sequences were synthesized and cloned into a mammalian expression plasmid, creating plasmid DNA constructs for expression of synthetic consensus antigens in vivo.
Figure 3:
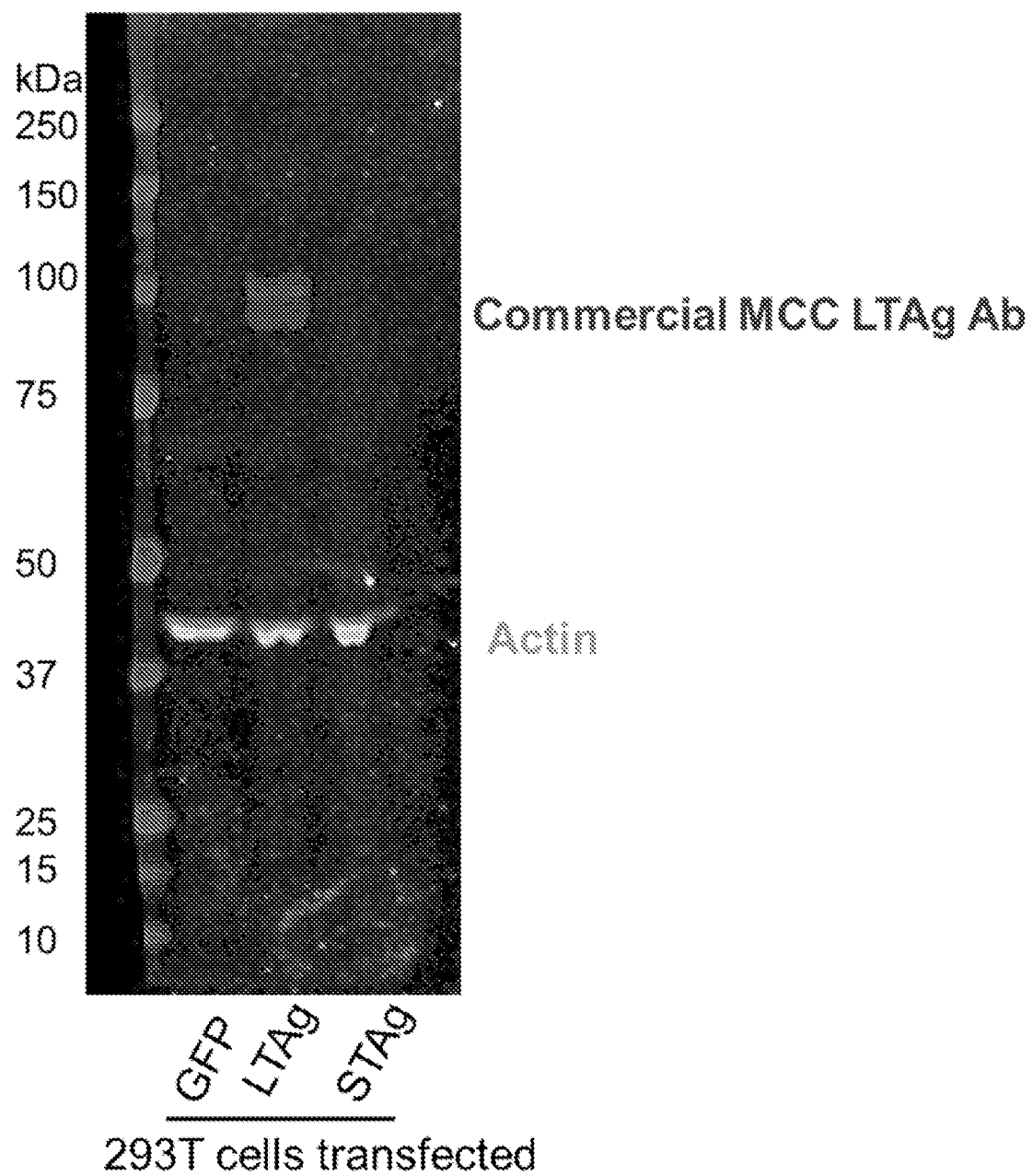
FIG. 3 depicts exemplary experimental data demonstrating expression of the consensus MCC LTAg in vitro. Expression of the consensus MCC STAg was not detected due to the lack of an effective antibody targeting the STAg.
Figures 4A, 4B:
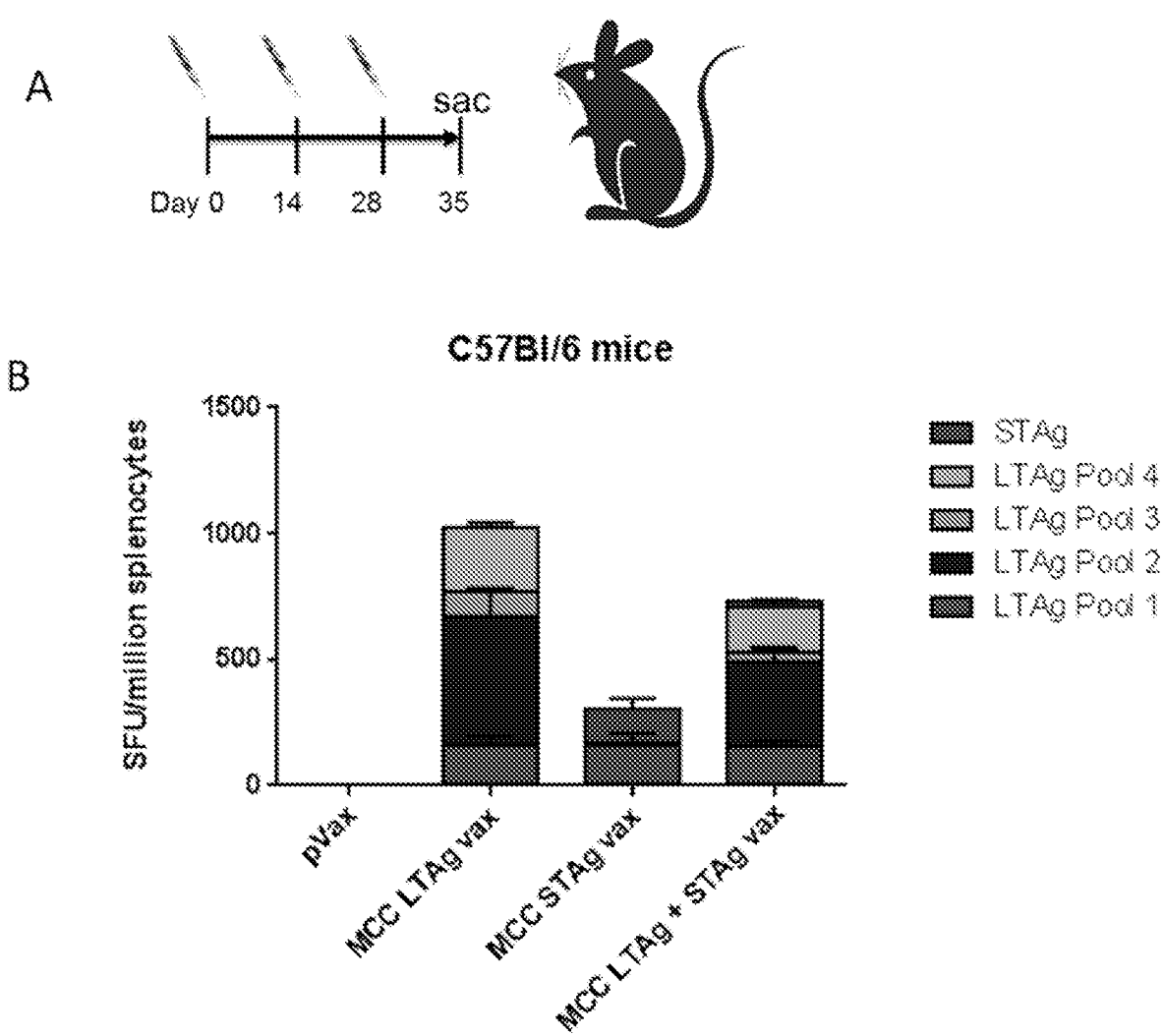
FIG. 4A depicts the experimental design. Mice received plasmid DNA followed by intramuscular electroporation at day 0, day 14 and day 28. One week later, splenocytes were collected for analysis. Four groups of mice were vaccinated: group 1—pVax-empty vector control; group 2—LTAg vaccine; group 3—STAg vaccine; group 4—LTAg and STAg vaccine at same site.
FIG. 4B depicts experimental data showing that an induction of an immune response following vaccination with LTAg and STAg alone or in combination, but not following vaccination with an empty control vector (pVax). For these experiments, the peptides were matched to the corresponding sequences without inactivating mutations.
Figures 5A, 5B:
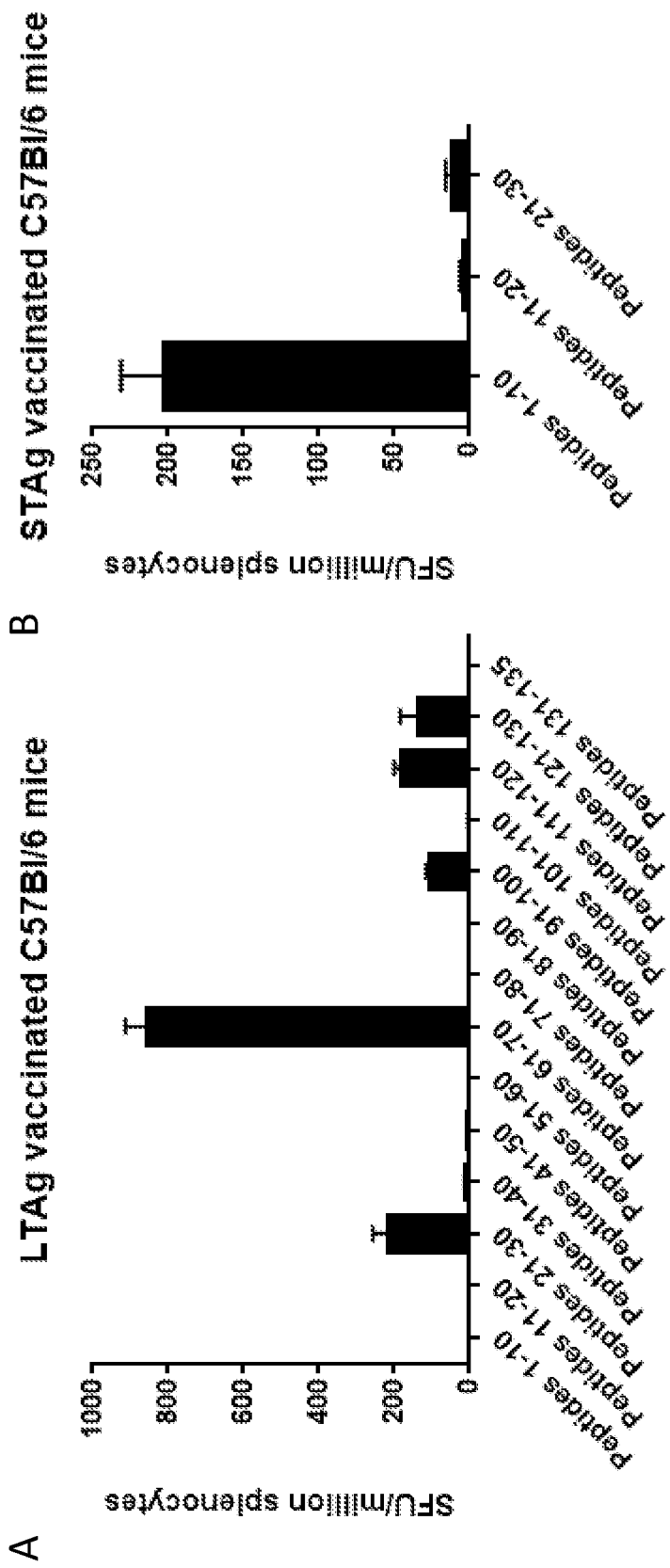
FIG. 5A depicts the immunodominant epitopes for LTAg vaccination.
FIG. 5B depicts the immunodominant epitopes for STAg vaccination.
Figure 6:
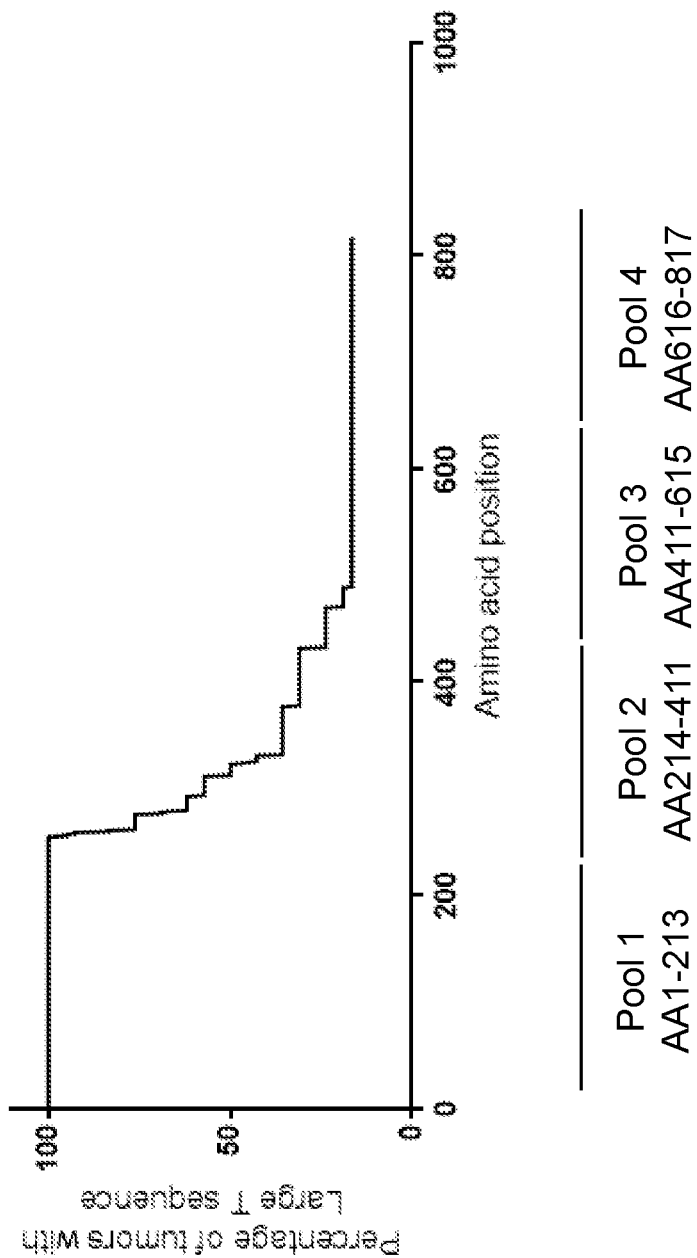
FIG. 6 depicts the results on an analysis of the extent of MCC Large T truncation in human Merkel cell carcinoma samples. Data was compiled from 42 Large T sequences in GenBank.
Figures 7A, 7B, 7C, 7D, 7E, 7F:
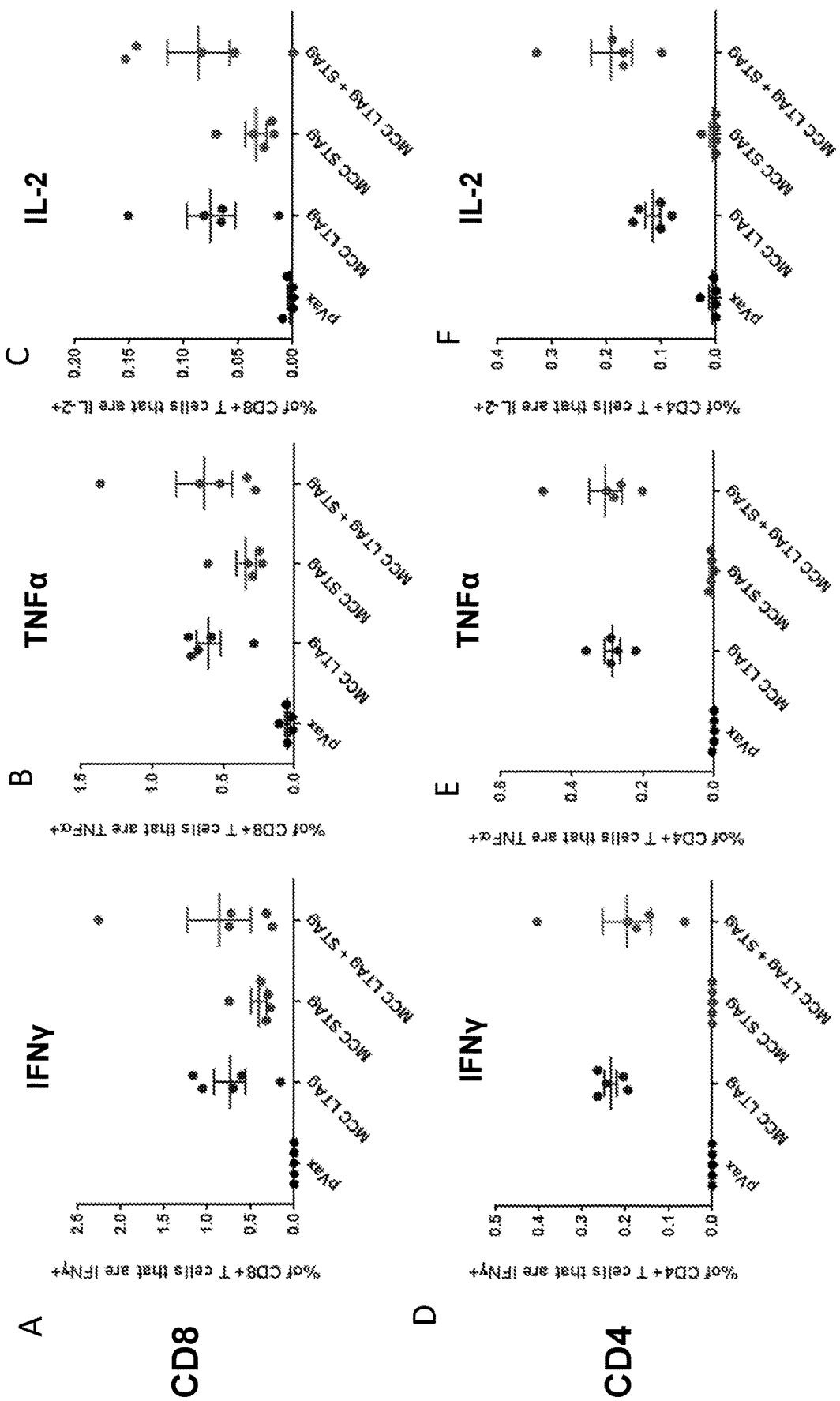
FIG. 7A depicts the levels of CD8$^+$ T cell response for IFNγ.
FIG. 7B depicts the levels of CD8$^+$ T cell response for TNFα.
FIG. 7C depicts the levels of CD8$^+$ T cell response for IL-2.
FIG. 7D depicts the levels of CD4$^+$ T cell response for IFNγ.
FIG. 7E depicts the levels of CD4$^+$ T cell response for TNFα.
FIG. 7F depicts the levels of CD4$^+$ T cell response for IL-2.

A nucleic acid vaccine targeting Merkel Cell Polyomavirus (MCV) T antigens has been developed (FIG. 1 and FIG. 2). Optimized synthetic consensus MCV T antigen sequences representing the large T antigen (LTAg) and small t antigen (STAg) were individually cloned into mammalian expression-plasmid DNA (FIG. 3) and delivered to mice via intramuscular electroporation (FIG. 4A). Following immunization, DNA vaccine constructs generated robust antibody and T-cell responses against MCV T antigen peptides (FIG. 4B through FIG. 15).

Figure 8:
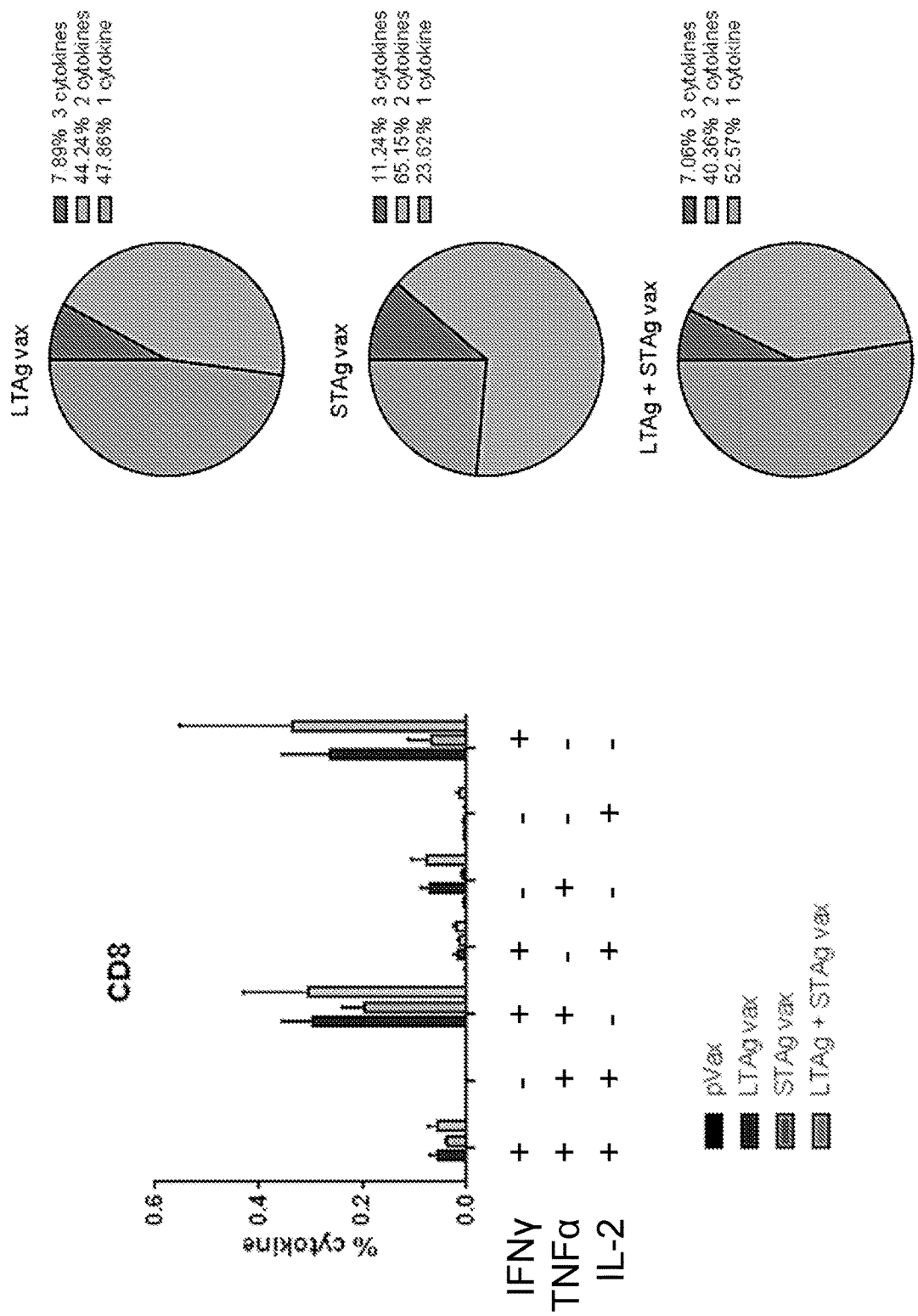
FIG. 8 depicts exemplary experimental data demonstrating that LTAg vaccination induces robust polyfunctional CD8 T cells.
Figure 9:
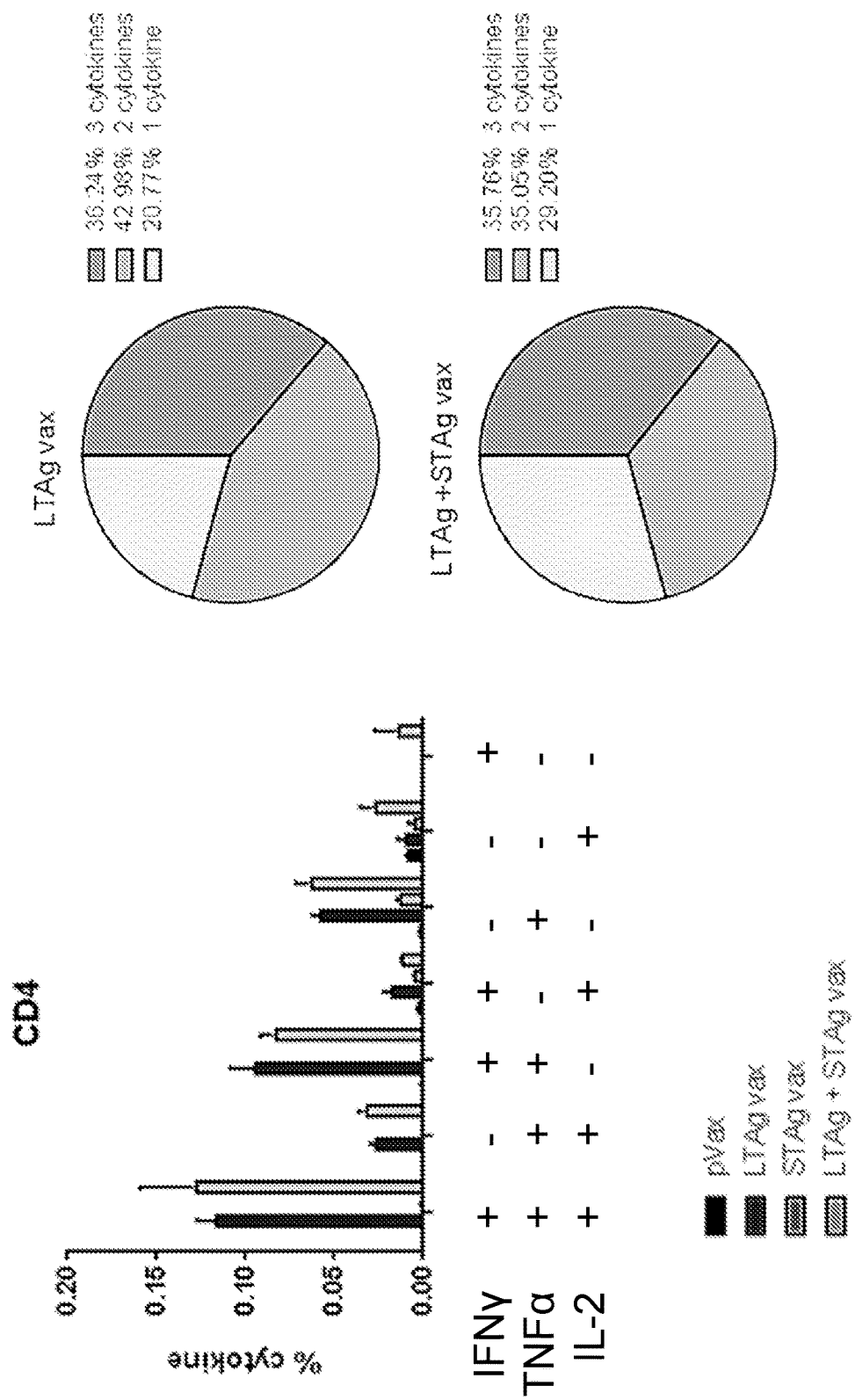
FIG. 9 depicts exemplary experimental data demonstrating that LTAg vaccination induces robust polyfunctional CD4 T cells.
Figure 10:
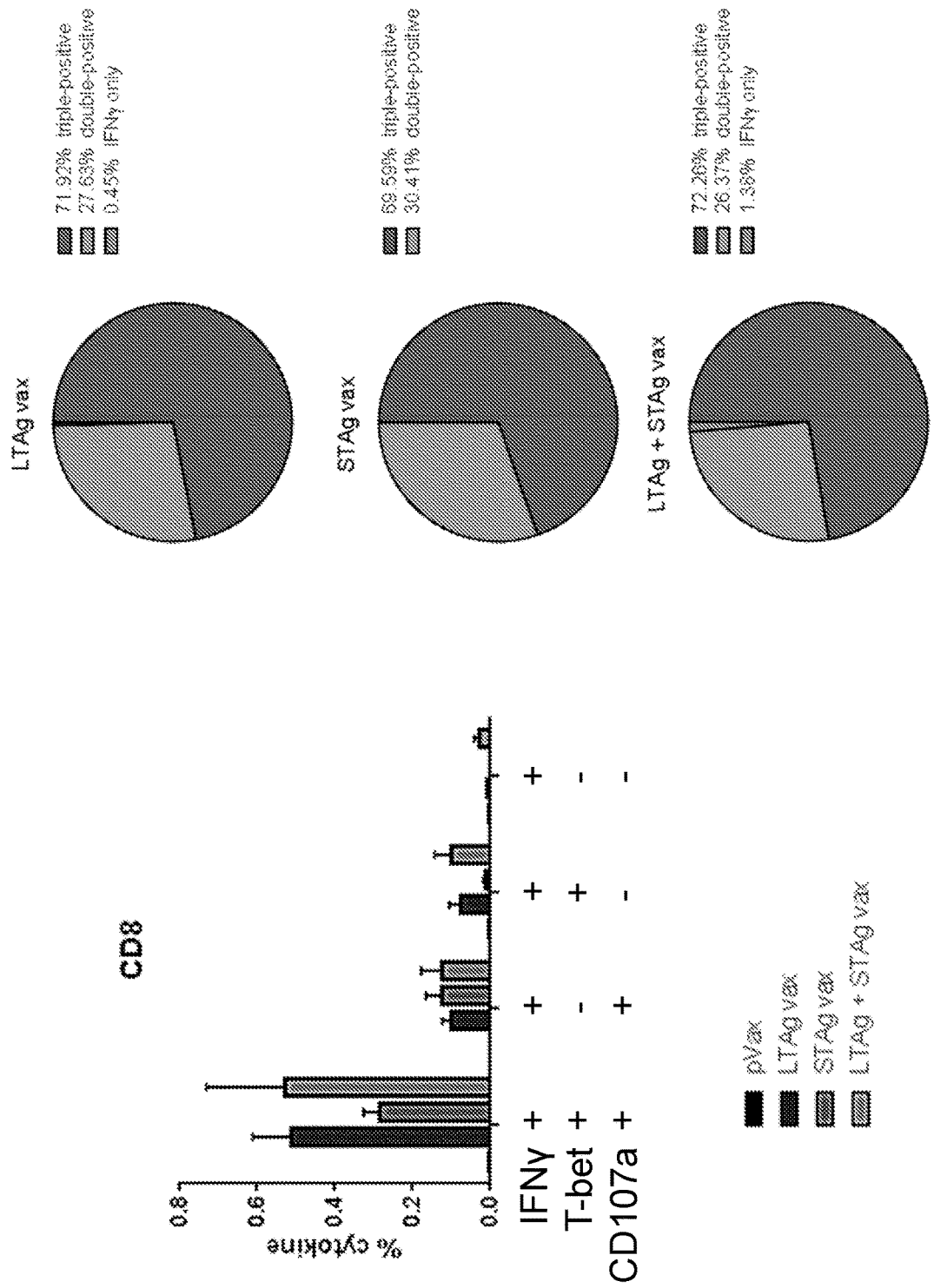
FIG. 10 depicts exemplary experimental data demonstrating that LTAg vaccination induces CD8 T cells with cytotoxic potential that co-express CD107a, IFNγ and T-bet.

FIG. 4B, FIG. 7, FIG. 12 and FIG. 14 demonstrate that the LTAg vaccine is highly immunogenic in C57Bl/6 and CD-1 outbred mice. FIG. 8 through FIG. 10 demonstrate that LTAg vaccination results in robust, polyfunctional CD4 and CD8 T cells and cytotoxic CD8 T cells.

Figures 15A, 15B, 15C, 15D, 15E, 15F:
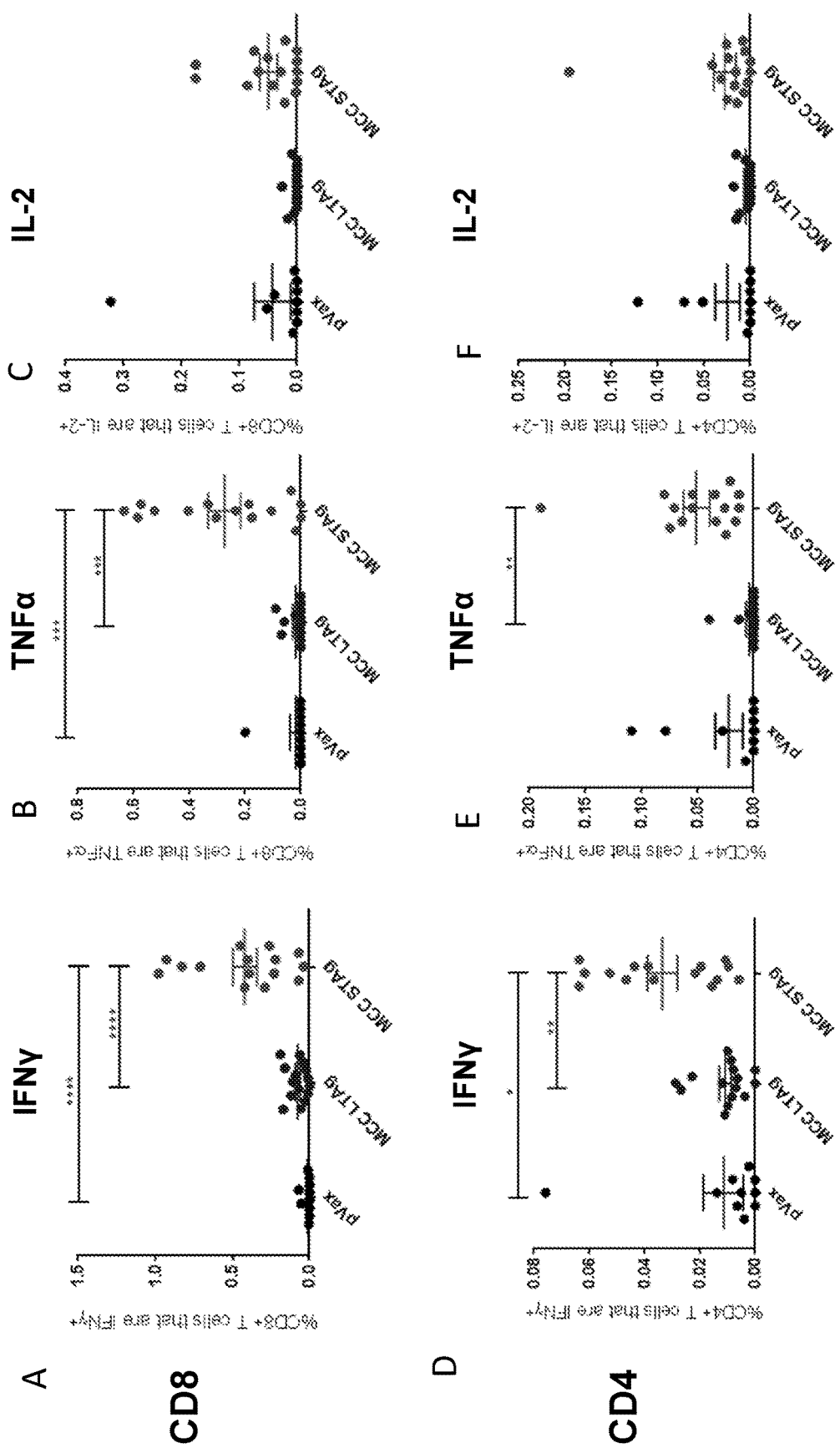
FIG. 15A depicts the levels of CD8$^+$ T cell response for IFNγ.
FIG. 15B depicts the levels of CD8$^+$ T cell response for TNFα.
FIG. 15C depicts the levels of CD8$^+$ T cell response for IL-2.
FIG. 15D depicts the levels of CD4$^+$ T cell response for IFNγ.
FIG. 15E depicts the levels of CD4$^+$ T cell response for TNFα.
FIG. 15F depicts the levels of CD4$^+$ T cell response for IL-2.

FIG. 4B and FIG. 15 demonstrate that STAg vaccine is immunogenic in C57Bl/6 and CD-1 mice. FIG. 15 demonstrates that both CD4 and CD8 responses were detected for IFNγ/TNFα for CD-1 mice.

Figure 11:
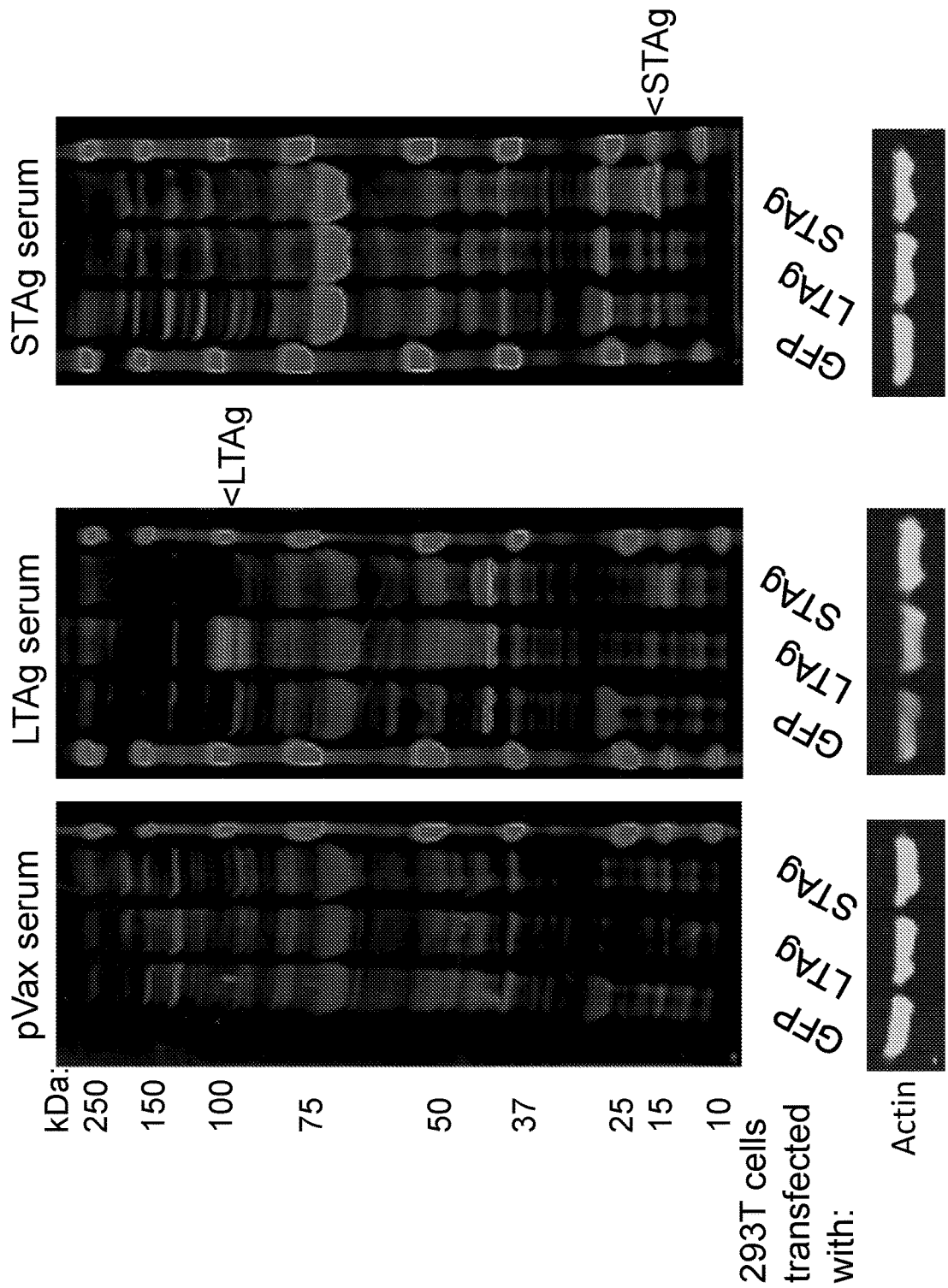
FIG. 11 depicts exemplary experimental data demonstrating that Large T and Small T antigen vaccines generate humoral responses, demonstrated using mouse serum as a primary antibody.
Figure 12:
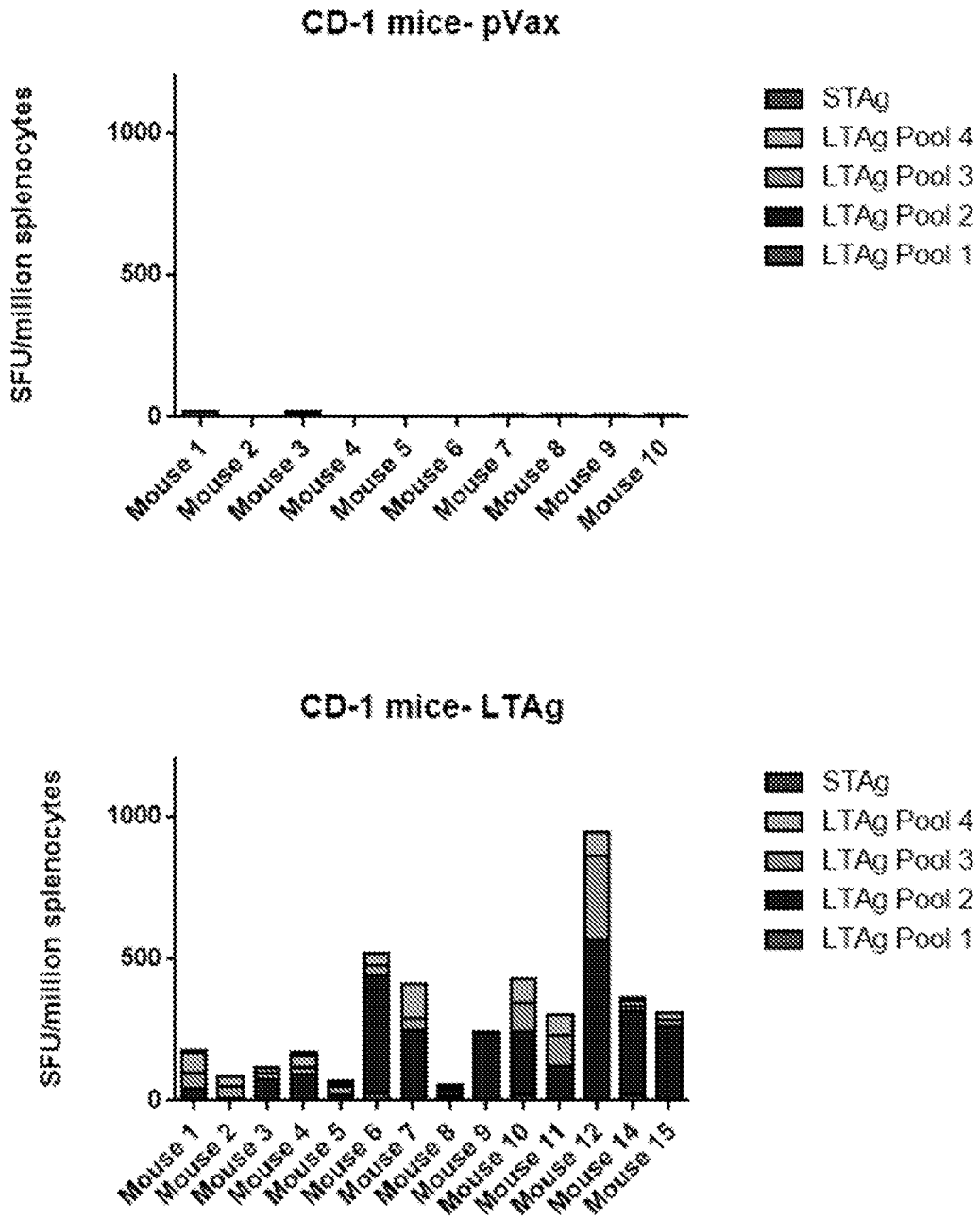
FIG. 12 depicts exemplary experimental data demonstrating that the LTAg vaccine induces robust immune responses in genetically diverse, CD-1 outbred mice.
Figure 13:
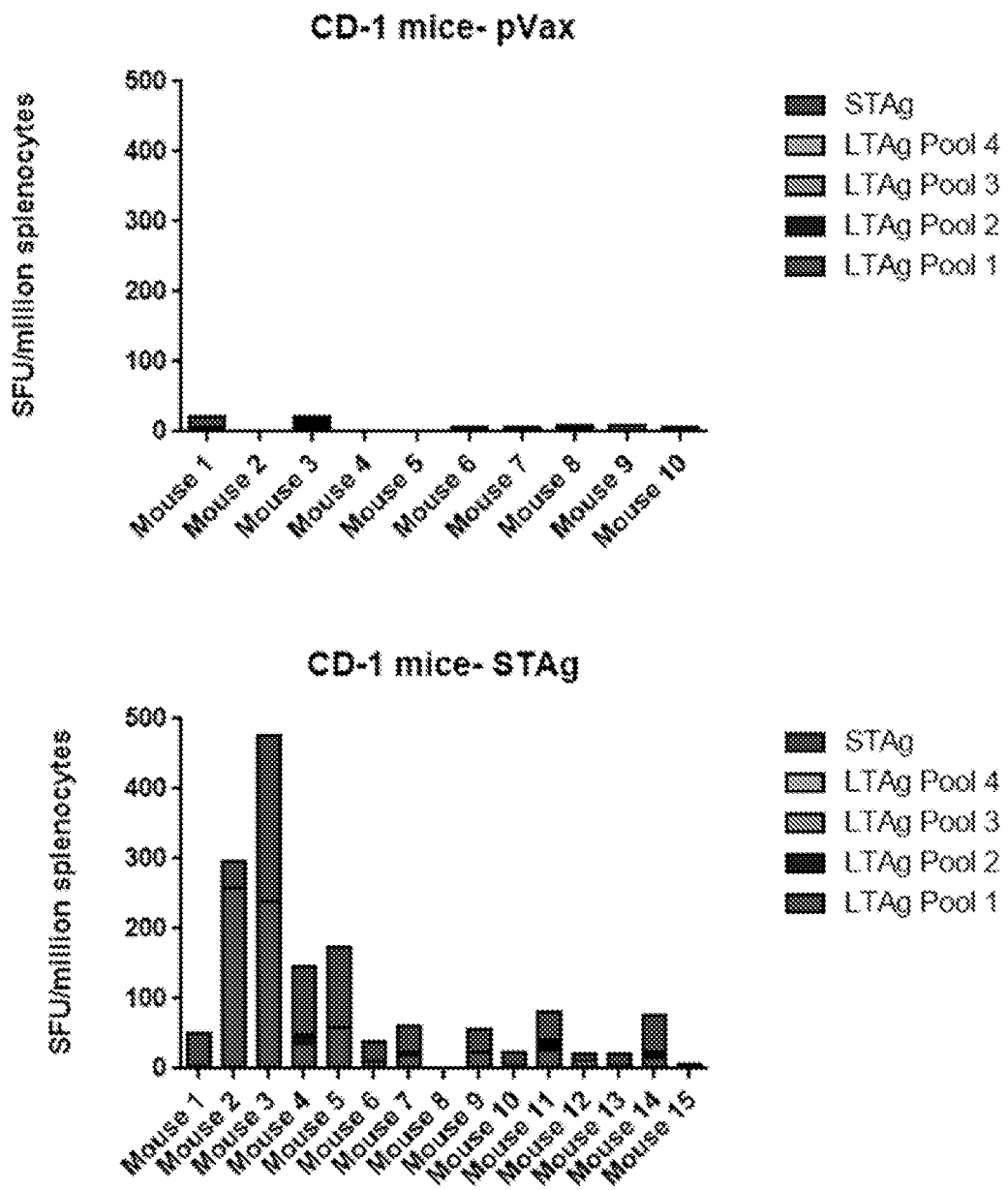
FIG. 13 depicts exemplary experimental data demonstrating that the STAg vaccine induces immune responses in genetically diverse, CD-1 outbred mice.
Figures 14A, 14B, 14C, 14D, 14E, 14F:
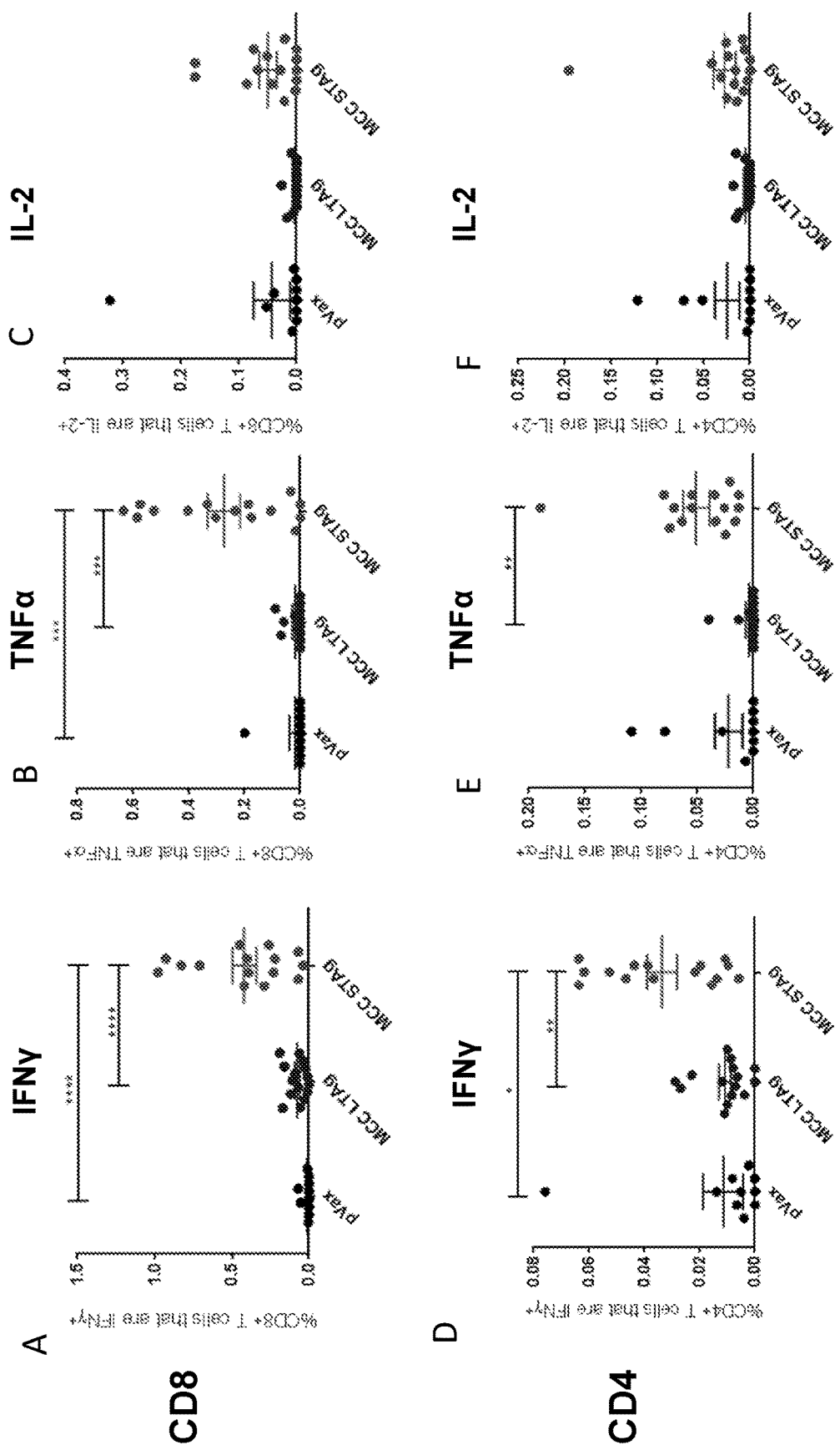
FIG. 14A depicts the levels of CD8$^+$ T cell response for IFNγ.
FIG. 14B depicts the levels of CD8$^+$ T cell response for TNFα.
FIG. 14C depicts the levels of CD8$^+$ T cell response for IL-2.
FIG. 14D depicts the levels of CD4$^+$ T cell response for IFNγ.
FIG. 14E depicts the levels of CD4$^+$ T cell response for TNFα.
FIG. 14F depicts the levels of CD4$^+$ T cell response for IL-2.

FIG. 11 demonstrates that both vaccines generate humoral response in C57Bl/6 mice.

Example 2: Sequences

```
SEQ ID NO: 1:
Nucleotide sequence encoding modified synthetic consensus MCV LTAg
ATGGACCTGGTGCTGAACAGGAAGGAGAGAGAGGCCCTGTGCAAGCTGCTGGAG

ATCGCCCCCAACTGTTACGGCAATATCCCTCTGATGAAGGCCGCCTTCAAGCGGA

GCTGCCTGAAGCACCACCCCAACAAGGGCGGCAACCCTGTGATCATGATGGAGC

TGAATACCCTGTGGTCCAAGTTTCAGCAGAATATCCACAAGCTGCGGTCCGATTT

CTCTATGTTTGACGAGGTGGATGAGGCCCCTATCTACGGCACCACCAAGTTCAAG

GAGTGGTGGCGCTCCGGCGGCTTCTCTTTTGGCAAGGCCTACGAGTACGGCCCTA

ACCCACACGGCACCAATAGCAGGTCCAGAAAGCCAAGCTCCAACGCCAGCAGGG

GAGCACCATCCGGATCTAGCCCACCTCACAGCCAGTCCTCTAGCTCCGGCTACGG

CTCTTTTAGCGCCTCCCAGGCCTCTGACAGCCAGTCCAGAGGCCCCGATATCCCA

CCCGAGCACCACGAGGAGCCTACCTCTAGCTCCGGCTCTAGCTCCCGGGAGGAG

ACAACCAACAGCGGCAGGGAGTCTAGCACCCCAAACGGCACCTCCGTGCCAAGG

AATTCCTCTAGGACCGACGGAACCGCCGAGGACCTGTTCTGCGATAAGTCCCTGA

GCTCCCCTGAGCCTCCATCTAGCTCCGAGGAGCCAGAGGAGCCCCCTTCTAGCAG

GTCCTCTCCCAGACAGCCACCAAGCTCCTCTGCCGAGGAGGCAAGCTCCTCTCAG

TTCACCGACGAGGAGTACAGGAGCTCCTCTTTTACCACCCCTAAGACCCCTCCAC

CCTTCTCCCGGAAGCGCAAGTTTGGAGGCTCTAGGAGCTCCGCCTCTAGCGCCTC

CTCTGCCAGCTTCACCTCCACCCCTCCAAAGCCCAAGAAGAACAGAGAGACACC

CGTGCCTACCGACTTTCCTATCGACCTGAGCGATTACCTGTCCCACGCCGTGTAC

TCTAATAAGACCGTGAGCTGTTTCGCCATCTACACCACCAGCGACAAGGCCATCG

AGCTGTACGATAAGATCGAGAAGTTCAAGGTGGACTTCAAGTCCAGGCACGCAT

GCGAGCTGGGATGTATCCTGCTGTTCATCACCCTGTCCAAGCACCGCGTGTCTGC

CATCAAGAACTTCTGCAGCACCTTTTGTACCATCTCCTTTCTGATCTGCAAGGGCG

TGAATAAGATGCCTGAGATGTACAACAACCTGTGCAAGCCCCCTTACAAGCTGCT

GCAGGAGAACAAGCCACTGCTGAATTACGAGTTCCAGGAGAAGGAGAAGGAGG

CCAGCTGCAACTGGAATCTGGTGGCCGAGTTCGCCTGTGAGTACGAGCTGGACG

ATCACTTTATCATCCTGGCCCACTACCTGGACTTCGCCAAGCCATTTCCCTGCCAG
```

-continued
```
AAGTGTGAGAACAGGTCTAGACTGAAGCCACACAAGGCCCACGAGGCCCACCAC

TCCAATGCCAAGCTGTTTTACGAGTCTAAGAGCCAGAAGACCATCTGCCAGCAG

GCAGCAGACACCGTGCTGGCAAAGAGGAGACTGGAGATGCTGGAGATGACCAG

GACCGAGATGCTGTGCAAGAAGTTCAAGAAGCACCTGGAGCGGCTGCGCGACCT

GGATACCATCGATCTGCTGTACTACATGGGCGGCGTGGCCTGGTACTGCTGTCTG

TTCGAGGAGTTTGAGAAGAAGCTGCAGAAGATCATCCAGCTGCTGACCGAGAAC

ATCCCAAAGTACAGAAATATCTGGTTCAAGGGCCCCATCAACTCTGGCAAGACC

AGCTTCGCCGCCGCCCTGATCGACCTGCTGGAGGGCAAGGCCCTGAACATCAATT

GCCCTAGCGATAAGCTGCCATTCGAGCTGGGCTGTGCCCTGGACAAGTTCATGGT

GGTGTTTGAGGATGTGAAGGGCCAGAACTCCCTGAATAAGGACCTGCAGCCCGG

CCAGGGCATCAACAATCTGGATAACCTGCGGGACCACCTGGATGGAGCAGTGGC

CGTGAGCCTGGAGAAGAAGCACGTGAACAAGAAGCACCAGATCTTCCCACCCTG

CATCGTGACCGCCAATGACTACTTTATCCCAAAGACCCTGATCGCCCGCTTCTCT

TACACCCTGCACTTTAGCCCCAAGGCCAACCTGAGGGACAGCCTGGATCAGAAT

ATGGAGATCAGAAAGAGGCGCATCCTGCAGTCCGGAACCACCCTGCTGCTGTGC

CTGATCTGGTGTCTGCCTGACACCACCTTCAAGCCATGCCTGCAGGAGGAGATCA

AGAACTGGAAGCAGATCCTGCAGTCTGAGATCAGCTACGGCAAGTTTTGTCAGA

TGATCGAGAACGTGGAGGCCGGCCAGGACCCCCTGCTGAATATCCTGATCGAGG

AGGAGGGCCCAGAGGAGACAGAGGAGACACAGGACTCCGGCACCTTCTCTCAG
```

SEQ ID NO: 2:
Amino acid sequence of modified synthetic consensus MCV LTAg
```
MDLVLNRKEREALCKLLEIAPNCYGNIPLMKAAFKRSCLKHHPNKGGNPVIMMELN

TLWSKFQQNIHKLRSDFSMFDEVDEAPIYGTTKFKEWWRSGGFSFGKAYEYGPNPH

GTNSRSRKPSSNASRGAPSGSSPPHSQSSSSGYGSFSASQASDSQSRGPDIPPEHHEEPT

SSSGSSSREETTNSGRESSTPNGTSVPRNSSRTDGTAEDLFCDKSLSSPEPPSSSEEPEEP

PSSRSSPRQPPSSSAEEASSSQFTDEEYRSSSFTTPKTPPPFSRKRKFGGSRSSASSASSA

SFTSTPPKPKKNRETPVPTDFPIDLSDYLSHAVYSNKTVSCFAIYTTSDKAIELYDKIEK

FKVDFKSRHACELGCILLFITLSKHRVSAIKNFCSTFCTISFLICKGVNKMPEMYNNLC

KPPYKLLQENKPLLNYEFQEKEKEASCNWNLVAEFACEYELDDHFIILAHYLDFAKP

FPCQKCENRSRLKPHKAHEAHHSNAKLFYESKSQKTICQQAADTVLAKRRLEMLEM

TRTEMLCKKFKKHLERLRDLDTIDLLYYMGGVAWYCCLFEEFEKKLQKIIQLLTENI

PKYRNIWFKGPINSGKTSFAAALIDLLEGKALNINCPSDKLPFELGCALDKFMVVFED

VKGQNSLNKDLQPGQGINNLDNLRDHLDGAVAVSLEKKHVNKKHQIFPPCIVTAND

YFIPKTLIARFSYTLHFSPKANLRDSLDQNMEIRKRRILQSGTTLLLCLIWCLPDTTFKP

CLQEEIKNWKQILQSEISYGKFCQMIENVEAGQDPLLNILIEEEGPEETEETQDSGTFSQ
```

SEQ ID NO: 3:
Nucleotide sequence encoding modified synthetic consensus MCV STAg
```
ATGGACCTGGTGCTGAACCGAAAGGAGAGGGAGGCCCTGTGCAAGCTGCTGGAG

ATCGCCCCTAACTGTTACGGCAATATCCCACTGATGAAGGCCGCCTTCAAGAGGT

CTTGCCTGAAGCACCACCCAAACAAGGGCGGCAATCCCGTGATCATGATGGAGC

TGAACACCCTGTGGAGCAAGTTTCAGCAGAATATCCACAAGCTGCGGAGCGACT

TCTCCATGTTTGATGAGGTGAGCACCAAGTTCCCCTGGGAGGAGTACGGAACAG

CAGCAGCAGCAGCACAGTCCGGCTATAACGCCAGGTTTTGCAGAGGCCCTGGCT
```

-continued
GTATGCTGAAGCAGCTGCGGGACTCCAAGTGCGCCTGTATCTCTTGCAAGCTGAG

CCGCCAGCACTGTTCTCTGAAGACCCTGAAGCAGAAGAATTGCGCCACATGGGG

CGAGTGCTTCTGTTATCAGTGTTTTATCCTGTGGTTCGGCTTTCCCCCTACATGGG

AGTCCTTCGATTGGTGGCAGAAAACCCTGGAAGAAACCGACTACTGTCTGCTGCA

TCTGCATCTGTTC

SEQ ID NO: 4:
Amino acid sequence of modified synthetic consensus MCV STAg
MDLVLNRKEREALCKLLEIAPNCYGNIPLMKAAFKRSCLKHHPNKGGNPVIMMELN

TLWSKFQQNIHKLRSDFSMFDEVSTKFPWEEYGTAAAAAQSGYNARFCRGPGCMLK

QLRDSKCACISCKLSRQHCSLKTLKQKNCATWGECFCYQCFILWFGFPPTWESFDW

WQKTLEETDYCLLHLHLF

SEQ ID NO: 5:
Nucleotide sequence encoding modified synthetic consensus LTAg
and STAg linked with a furin cleavage site
ATGGACCTGGTGCTGAACAGGAAGGAGAGAGAGGCCCTGTGCAAGCTGCTGGAG

ATCGCCCCCAACTGTTACGGCAATATCCCTCTGATGAAGGCCGCCTTCAAGCGGA

GCTGCCTGAAGCACCACCCCAACAAGGGCGGCAACCCTGTGATCATGATGGAGC

TGAATACCCTGTGGTCCAAGTTTCAGCAGAATATCCACAAGCTGCGGTCCGATTT

CTCTATGTTTGACGAGGTGGATGAGGCCCTATCTACGGCACCACCAAGTTCAAG

GAGTGGTGGCGCTCCGGCGGCTTCTCTTTTGGCAAGGCCTACGAGTACGGCCCTA

ACCCACACGGCACCAATAGCAGGTCCAGAAAGCCAAGCTCCAACGCCAGCAGGG

GAGCACCATCCGGATCTAGCCCACCTCACAGCCAGTCCTCTAGCTCCGGCTACGG

CTCTTTTAGCGCCTCCCAGGCCTCTGACAGCCAGTCCAGAGGCCCCGATATCCCA

CCCGAGCACCACGAGGAGCCTACCTCTAGCTCCGGCTCTAGCTCCCGGGAGGAG

ACAACCAACAGCGGCAGGGAGTCTAGCACCCCAAACGGCACCTCCGTGCCAAGG

AATTCCTCTAGGACCGACGGAACCGCCGAGGACCTGTTCTGCGATAAGTCCCTGA

GCTCCCCTGAGCCTCCATCTAGCTCCGAGGAGCCAGAGGAGCCCCCTTCTAGCAG

GTCCTCTCCCAGACAGCCACCAAGCTCCTCTGCCGAGGAGGCAAGCTCCTCTCAG

TTCACCGACGAGGAGTACAGGAGCTCCTCTTTTACCACCCCTAAGACCCCTCCAC

CCTTCTCCCGGAAGCGCAAGTTTGGAGGCTCTAGGAGCTCCGCCTCTAGCGCCTC

CTCTGCCAGCTTCACCTCCACCCCTCCAAAGCCCAAGAAGAACAGAGAGACACC

CGTGCCTACCGACTTTCCTATCGACCTGAGCGATTACCTGTCCCACGCCGTGTAC

TCTAATAAGACCGTGAGCTGTTTCGCCATCTACACCACCAGCGACAAGGCCATCG

AGCTGTACGATAAGATCGAGAAGTTCAAGGTGGACTTCAAGTCCAGGCACGCAT

GCGAGCTGGGATGTATCCTGCTGTTCATCACCCTGTCCAAGCACCGCGTGTCTGC

CATCAAGAACTTCTGCAGCACCTTTTGTACCATCTCCTTTCTGATCTGCAAGGGCG

TGAATAAGATGCCTGAGATGTACAACAACCTGTGCAAGCCCCCTTACAAGCTGCT

GCAGGAGAACAAGCCACTGCTGAATTACGAGTTCCAGGAGAAGGAGAAGGAGG

CCAGCTGCAACTGGAATCTGGTGGCCGAGTTCGCCTGTGAGTACGAGCTGGACG

ATCACTTTATCATCCTGGCCCACTACCTGGACTTCGCCAAGCCATTTCCCTGCCAG

AAGTGTGAGAACAGGTCTAGACTGAAGCCACACAAGGCCCACGAGGCCCACCAC

TCCAATGCCAAGCTGTTTTACGAGTCTAAGAGCCAGAAGACCATCTGCCAGCAG

GCAGCAGACACCGTGCTGGCAAAGAGGAGACTGGAGATGCTGGAGATGACCAG

-continued

GACCGAGATGCTGTGCAAGAAGTTCAAGAAGCACCTGGAGCGGCTGCGCGACCT

GGATACCATCGATCTGCTGTACTACATGGGCGGCGTGGCCTGGTACTGCTGTCTG

TTCGAGGAGTTTGAGAAGAAGCTGCAGAAGATCATCCAGCTGCTGACCGAGAAC

ATCCCAAAGTACAGAAATATCTGGTTCAAGGGCCCCATCAACTCTGGCAAGACC

AGCTTCGCCGCCGCCCTGATCGACCTGCTGGAGGGCAAGGCCCTGAACATCAATT

GCCCTAGCGATAAGCTGCCATTCGAGCTGGGCTGTGCCCTGGACAAGTTCATGGT

GGTGTTTGAGGATGTGAAGGGCCAGAACTCCCTGAATAAGGACCTGCAGCCCGG

CCAGGGCATCAACAATCTGGATAACCTGCGGGACCACCTGGATGGAGCAGTGGC

CGTGAGCCTGGAGAAGAAGCACGTGAACAAGAAGCACCAGATCTTCCCACCCTG

CATCGTGACCGCCAATGACTACTTTATCCCAAAGACCCTGATCGCCCGCTTCTCT

TACACCCTGCACTTTAGCCCCAAGGCCAACCTGAGGGACAGCCTGGATCAGAAT

ATGGAGATCAGAAAGAGGCGCATCCTGCAGTCCGGAACCACCCTGCTGCTGTGC

CTGATCTGGTGTCTGCCTGACACCACCTTCAAGCCATGCCTGCAGGAGGAGATCA

AGAACTGGAAGCAGATCCTGCAGTCTGAGATCAGCTACGGCAAGTTTTGTCAGA

TGATCGAGAACGTGGAGGCCGGCCAGGACCCCCTGCTGAATATCCTGATCGAGG

AGGAGGGCCCAGAGGAGACAGAGGAGACACAGGACTCCGGCACCTTCTCTCAG

AGAGGCCGCAAAAGGAGGTCTGATCTGGTGCTGAATCGGAAAGAGAGAGAAGC

CCTGTGCAAACTGCTGGAAATCGCCCCAAACTGTTACGGCAACATCCCCCTGATG

AAGGCCGCCTTCAAGAGGTCTTGCCTGAAGCACCACCCAAACAAGGGCGGCAAT

CCCGTGATCATGATGGAGCTGAACACCCTGTGGAGCAAGTTTCAGCAGAATATCC

ACAAGCTGCGGAGCGACTTCTCCATGTTTGATGAGGTGAGCACCAAGTTCCCTTG

GGAGGAGTACGGAACAGCAGCAGCAGCAGCACAGTCCGGCTATAACGCCAGGTT

TTGCAGAGGCCCAGGCTGTATGCTGAAGCAGCTGCGGGACTCCAAGTGCGCCTG

TATCTCTTGCAAGCTGAGCCGCCAGCACTGTTCTCTGAAGACCCTGAAGCAGAAG

AATTGCGCCACATGGGGCGAGTGCTTCTGTTATCAGTGTTTTATCCTGTGGTTCGG

CTTTCCCCCTACATGGGAGTCCTTCGATTGGTGGCAGAAAACCCTGGAGGAAACT

GATTACTGTCTGCTGCACCTGCACCTGTTC

SEQ ID NO: 6:
Amino acid sequence of modified synthetic consensus LTAg and STAg linked with a furin cleavage site.
MDLVLNRKEREALCKLLEIAPNCYGNIPLMKAAFKRSCLKHHPNKGGNPVIMMELN

TLWSKFQQNIHKLRSDFSMFDEVDEAPIYGTTKFKEWWRSGGFSFGKAYEYGPNPH

GTNSRSRKPSSNASRGAPSGSSPPHSQSSSSGYGSFSASQASDSQSRGPDIPPEHHEEPT

SSSGSSSREETTNSGRESSTPNGTSVPRNSSRTDGTAEDLFCDKSLSSPEPPSSSEEPEEP

PSSRSSPRQPPSSSAEEASSSQFTDEEYRSSSFTTPKTPPPFSRKRKFGGSRSSASSASSA

SFTSTPPKPKKNRETPVPTDFPIDLSDYLSHAVYSNKTVSCFAIYTTSDKAIELYDKIEK

FKVDFKSRHACELGCILLFITLSKHRVSAIKNFCSTFCTISFLICKGVNKMPEMYNNLC

KPPYKLLQENKPLLNYEFQEKEKEASCNWNLVAEFACEYELDDHFIILAHYLDFAKP

FPCQKCENRSRLKPHKAHEAHHSNAKLFYESKSQKTICQQAADTVLAKRRLEMLEM

TRTEMLCKKFKKHLERLRDLDTIDLLYYMGGVAWYCCLFEEFEKKLQKIIQLLTENI

PKYRNIWFKGPINSGKTSFAAALIDLLEGKALNINCPSDKLPFELGCALDKFMVVFED

VKGQNSLNKDLQPGQGINNLDNLRDHLDGAVAVSLEKKHVNKKHQIFPPCIVTAND

-continued

YFIPKTLIARFSYTLHFSPKANLRDSLDQNMEIRKRRILQSGTTLLLCLIWCLPDTTFKP

CLQEEIKNWKQILQSEISYGKFCQMIENVEAGQDPLLNILIEEEGPEETEETQDSGTFS

QRGRKRRSDLVLNRKEREALCKLLEIAPNCYGNIPLMKAAFKRSCLKHHPNKGGNP

VIMMELNTLWSKFQQNIHKLRSDFSMFDEVSTKFPWEEYGTAAAAAQSGYNARFCR

GPGCMLKQLRDSKCACISCKLSRQHCSLKTLKQKNCATWGECFCYQCFILWFGFPPT

WESFDWWQKTLEETDYCLLHLHLF

SEQ ID NO: 7:
Amino acid sequence of IgE leader sequence
MDWTWILFLVAAATRVHS

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A nucleic acid molecule encoding at least one modified Merkel Cell Polyomavirus (MCV) T antigen, wherein the T antigen comprises at least one mutation that disrupts at least one oncogenic feature of a native MCV T antigen selected from the group consisting of CR1 binding, DnaJ binding, phophatase pp2A binding, Rb binding, ATPase activity, helicase activity, chaperone protein binding, hVam6p binding, Fbxw7 binding, origin binding, and transformation; wherein the nucleic acid molecule comprises a sequence selected from the group consisting of:
   a) a nucleotide sequence encoding an amino acid sequence comprising at least 98% identity to SEQ ID NO:4;
   b) a nucleotide sequence encoding an amino acid sequence comprising at least 90% identity to SEQ ID NO:6;
   c) a nucleotide sequence encoding an amino acid sequence selected from the group consisting of SEQ ID NO:4 and SEQ ID NO:6;
   d) a nucleotide sequence having at least about 90% identity over an entire length of a nucleotide sequence selected from the group consisting of SEQ ID NO:1, SEQ ID NO:3 and SEQ ID NO:5; and
   e) a nucleotide sequence selected from the group consisting of SEQ ID NO:1, SEQ ID NO:3 and SEQ ID NO:5.

2. The nucleic acid molecule of claim 1, wherein at least one mutation is a mutation at an amino acid selected from the group consisting of D44, W209, E216, L142, L91, K92, D93, Y94 and M95.

3. The nucleic acid molecule of claim 1, wherein at least one mutation is selected from the group consisting of a D44N mutation, a W209A, an E216K mutation, an L142A mutation, an L91A mutation, a K92A mutation, a D93A mutation, a Y94A mutation and a M95A mutation.

4. The nucleic acid molecule of claim 1, wherein the MCV T antigen is selected from the group consisting of a large T antigen (LTAg), a small t antigen (STAg), and a combination thereof.

5. The nucleic acid molecule of claim 1, wherein the nucleic acid molecule is selected from the group consisting of a DNA molecule and an RNA molecule.

6. The nucleic acid molecule of claim 1, wherein the nucleic acid molecule comprises
   a nucleotide sequence selected from the group consisting of SEQ ID NO:1, SEQ ID NO:3 and SEQ ID NO:5.

7. The nucleic acid molecule of claim 1, wherein the encoded peptide is operably linked to at least one regulatory sequence selected from the group consisting of a start codon, an IgE leader sequence and a stop codon.

8. The nucleic acid molecule of claim 7, wherein the nucleic acid molecule comprises a sequence selected from the group consisting of:
   a) a nucleotide sequence encoding an amino acid sequence comprising at least 98% identity to SEQ ID NO:4,
   b) a nucleotide sequence encoding an amino acid sequence comprising at least 90% identity to SEQ ID NO:6,
   c) a nucleotide sequence encoding an amino acid sequence selected from the group consisting of SEQ ID NO:4 and SEQ ID NO:6,
   d) a nucleotide sequence having at least about 90% identity over an entire length of a nucleotide sequence selected from the group consisting of SEQ ID NO:1, SEQ ID NO:3 and SEQ ID NO:5; and
   e) a nucleotide sequence selected from the group consisting of SEQ ID NO:1, SEQ ID NO:3 and SEQ ID NO:5,
   operably linked to an amino acid sequence as set forth in SEQ ID NO:7.

9. The nucleic acid molecule of claim 7, wherein the nucleic acid molecule comprises
   a nucleotide sequence selected from the group consisting of SEQ ID NO:1, SEQ ID NO:3 and SEQ ID NO:5,
   operably linked to a nucleotide sequence encoding SEQ ID NO:7.

10. The nucleic acid molecule of claim 1, wherein the nucleic acid molecule comprises an expression vector.

11. The nucleic acid molecule of claim 1, wherein the nucleic acid molecule comprises a viral particle.

12. An immunogenic composition comprising at least one nucleic acid molecule of claim 1.

13. The immunogenic composition of claim 12, further comprising at least one selected from the group consisting of a pharmaceutically acceptable excipient and an adjuvant.

14. A method of inducing an immune response against a MCV T antigen in a subject in need thereof, the method comprising administering an immunogenic composition of claim 12 to the subject.

15. A method of treating or preventing a MCV associated pathology in subject in need thereof, the method comprising administering an immunogenic composition of claim 1 to the subject.

16. The method of claim 15, wherein the MCV associated pathology is at least one of MCV infection and Merkel Cell Carcinoma.

17. A peptide comprising an amino acid sequence selected from the group consisting of
   a) an amino acid sequence comprising at least 98% identity to SEQ ID NO:4;
   b) an amino acid sequence comprising at least 90% identity to SEQ ID NO:6; and c) an amino acid sequence selected from the group consisting of SEQ ID NO:4 and SEQ ID NO:6.

18. An immunogenic composition comprising a peptide of claim 17.

* * * * *